US012661255B2

(12) United States Patent
Walls et al.

(10) Patent No.: US 12,661,255 B2
(45) Date of Patent: Jun. 23, 2026

(54) DETERMINING A VALUE INDICATIVE OF A THERMOREGULATORY ACTIVITY OF A PATIENT USING A TEMPERATURE MANAGEMENT SYSTEM

(71) Applicant: Zoll Circulation, Inc., San Jose, CA (US)

(72) Inventors: George L. Walls, San Jose, CA (US); Richard A. Helkowski, Redwood City, CA (US); Jeremy Thomas Dabrowiak, Santa Clara, CA (US); Byron Reynolds, San Jose, CA (US); Iljong Lee, Saratoga, CA (US); Michael W. Dae, San Mateo, CA (US); Sean W. Yip, Mountain View, CA (US)

(73) Assignee: Zoll Circulation, Inc., San Jose, CA (US)

( * ) Notice: Subject to any disclaimer, the term of this patent is extended or adjusted under 35 U.S.C. 154(b) by 811 days.

(21) Appl. No.: 17/796,379

(22) PCT Filed: Feb. 4, 2021

(86) PCT No.: PCT/US2021/016590
§ 371 (c)(1),
(2) Date: Jul. 29, 2022

(87) PCT Pub. No.: WO2021/158775
PCT Pub. Date: Aug. 12, 2021

(65) Prior Publication Data
US 2023/0142802 A1 May 11, 2023

Related U.S. Application Data

(60) Provisional application No. 62/970,123, filed on Feb. 4, 2020.

(51) Int. Cl.
A61F 7/00 (2006.01)
A61F 7/08 (2006.01)
(Continued)

(52) U.S. Cl.
CPC .............. *A61F 7/0085* (2013.01); *A61F 7/08* (2013.01); *G16H 40/63* (2018.01);
(Continued)

(58) Field of Classification Search
CPC ...... A61F 2007/0093; A61F 2007/0095; A61F 2007/0096; A61F 2007/126; A61F 7/0085; A61F 7/08; A61F 7/12; G16H 40/63
See application file for complete search history.

(56) References Cited

U.S. PATENT DOCUMENTS 9,241,827 B2 1/2016 Lim et al.
9,314,370 B2 4/2016 Dabrowiak et al.
(Continued)

FOREIGN PATENT DOCUMENTS

EP 3366199 A1 8/2018
JP 2003-506385 2/2003
(Continued)

OTHER PUBLICATIONS

JP Office Action in Japanese Appln. No. 2022-546581 mailed on Mar. 18, 2025, 8 pages (with English translation).
(Continued)

*Primary Examiner* — Tigist S Demie
(74) *Attorney, Agent, or Firm* — Fish & Richardson P.C.

(57) ABSTRACT

A temperature management system controls a temperature of a body of a patient and determines a value indicative of a thermoregulatory activity of the patient. The system includes a heat exchange system configured to exchange heat with a body of a patient and to record operational data
(Continued)

while controlling the temperature of the body of the patient. The temperature management system receives temperature data from a sensor, controls the heat exchange system to maintain the temperature of the body of the patient within a target temperature range, receives, in response to the controlling, operational data, determines, based on the temperature data and the operational data, a value indicative of a thermoregulatory activity of the patient, and generates, based on the value, an alert through the user interface indicating the thermoregulatory activity of the patient.

20 Claims, 14 Drawing Sheets

(51) Int. Cl.
  *G16H 40/63*          (2018.01)
  *A61F 7/12*           (2006.01)

(52) U.S. Cl.
  CPC ................. *A61F 2007/0054* (2013.01); *A61F 2007/0093* (2013.01); *A61F 2007/0096* (2013.01); *A61F 2007/126* (2013.01)

(56) References Cited

U.S. PATENT DOCUMENTS

|  |  |  |  |
|---|---|---|---|
| 9,433,526 | B2 | 9/2016 | Protasiewicz et al. |
| 9,492,633 | B2 | 11/2016 | Dabrowiak |
| 9,662,243 | B2 | 5/2017 | Dabrowiak |
| 9,717,625 | B2 | 8/2017 | Lim |
| 10,045,881 | B2 | 8/2018 | Helkowski et al. |
| 2003/0088299 | A1 | 5/2003 | Magers et al. |
| 2003/0167034 | A1 | 9/2003 | Balding |
| 2004/0073280 | A1 | 4/2004 | Dae et al. |
| 2004/0267339 | A1 | 12/2004 | Yon et al. |
| 2012/0109267 | A1 | 5/2012 | Fausset et al. |
| 2013/0090708 | A1 | 4/2013 | Dabrowiak et al. |
| 2014/0058277 | A1 | 2/2014 | Tan et al. |
| 2015/0238350 | A1 | 8/2015 | Tijs et al. |
| 2017/0354534 | A1* | 12/2017 | Paradis .................... A61F 7/12 |
| 2018/0185192 | A1 | 7/2018 | Mazzone et al. |
| 2018/0185193 | A1 | 7/2018 | Mazzone et al. |
| 2018/0207024 | A1 | 7/2018 | Dabrowiak et al. |
| 2018/0325725 | A1* | 11/2018 | Dabrowiak ............... A61F 7/12 |
| 2019/0083300 | A1 | 3/2019 | Machold et al. |
| 2024/0238117 | A1 | 7/2024 | Walls et al. |

FOREIGN PATENT DOCUMENTS

| | | |
|---|---|---|
| JP | 2004-538087 | 12/2004 |
| JP | 2011-504063 | 1/2011 |
| JP | 2013-248293 | 12/2013 |
| JP | 2019-509837 | 4/2019 |

OTHER PUBLICATIONS

PCT International Search Report and Written Opinion in International Appln. No. PCT/US2021/016590, dated Apr. 29, 2021, 10 pages.

PCT International Preliminary Report on Patentability in International Appln. No. PCT/US2021/016590, dated Aug. 18, 2022, 9 pages.

JP Office Action in Japanese Appln. No. 2022-546581, mailed on Aug. 27, 2024, 7 pages (with English translation).

EP Extended European Search Report in European Appln. No. 21750232.7, mailed on Jan. 22, 2024, 11 pages.

* cited by examiner

400

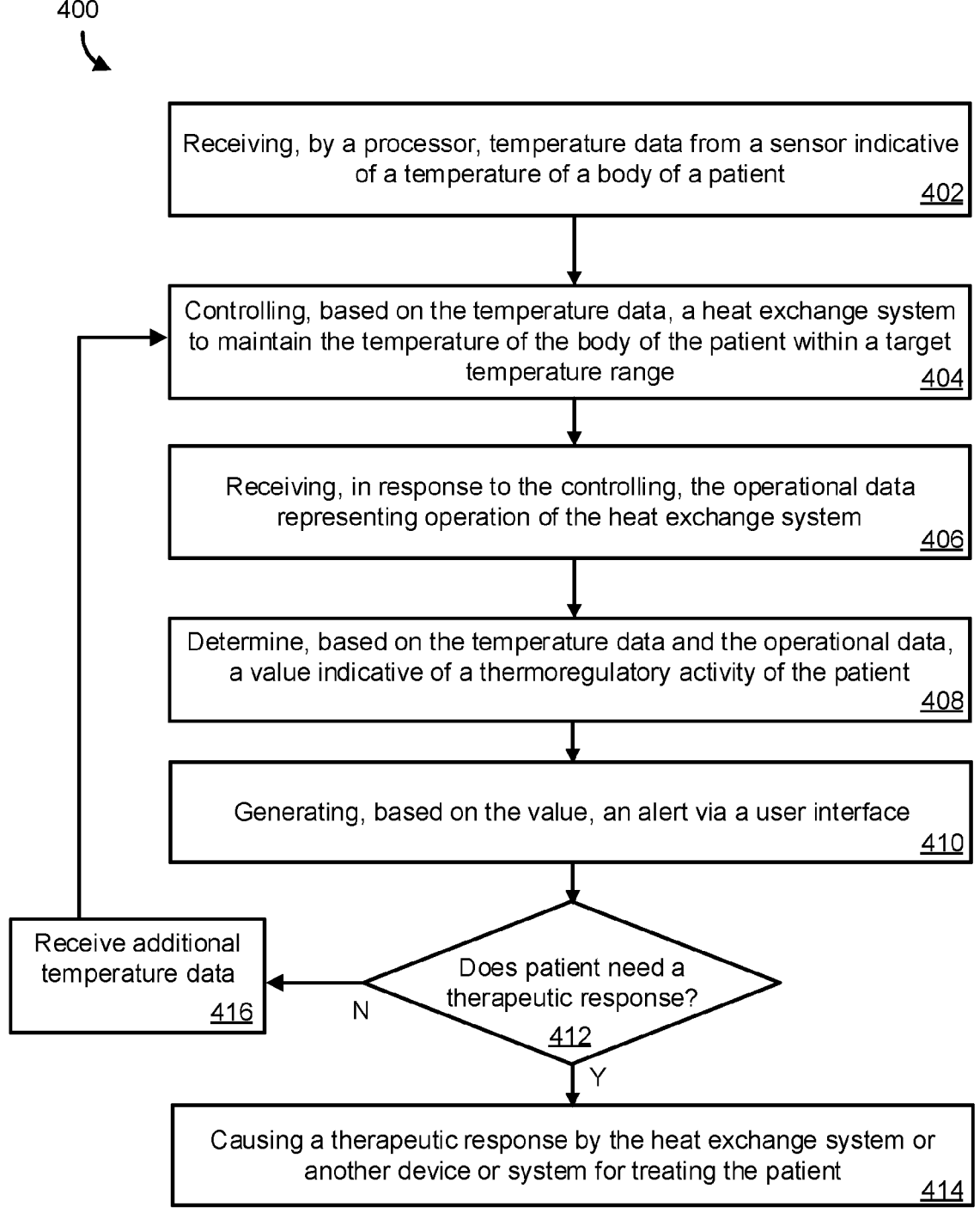

Receiving, by a processor, temperature data from a sensor indicative
of a temperature of a body of a patient
402

Controlling, based on the temperature data, a heat exchange system
to maintain the temperature of the body of the patient within a target
temperature range
404

Receiving, in response to the controlling, the operational data
representing operation of the heat exchange system
406

Determine, based on the temperature data and the operational data,
a value indicative of a thermoregulatory activity of the patient
408

Generating, based on the value, an alert via a user interface
410

Receive additional
temperature data
416

Does patient need a
therapeutic response?
412

N

Y

Causing a therapeutic response by the heat exchange system or
another device or system for treating the patient
414

FIG. 4

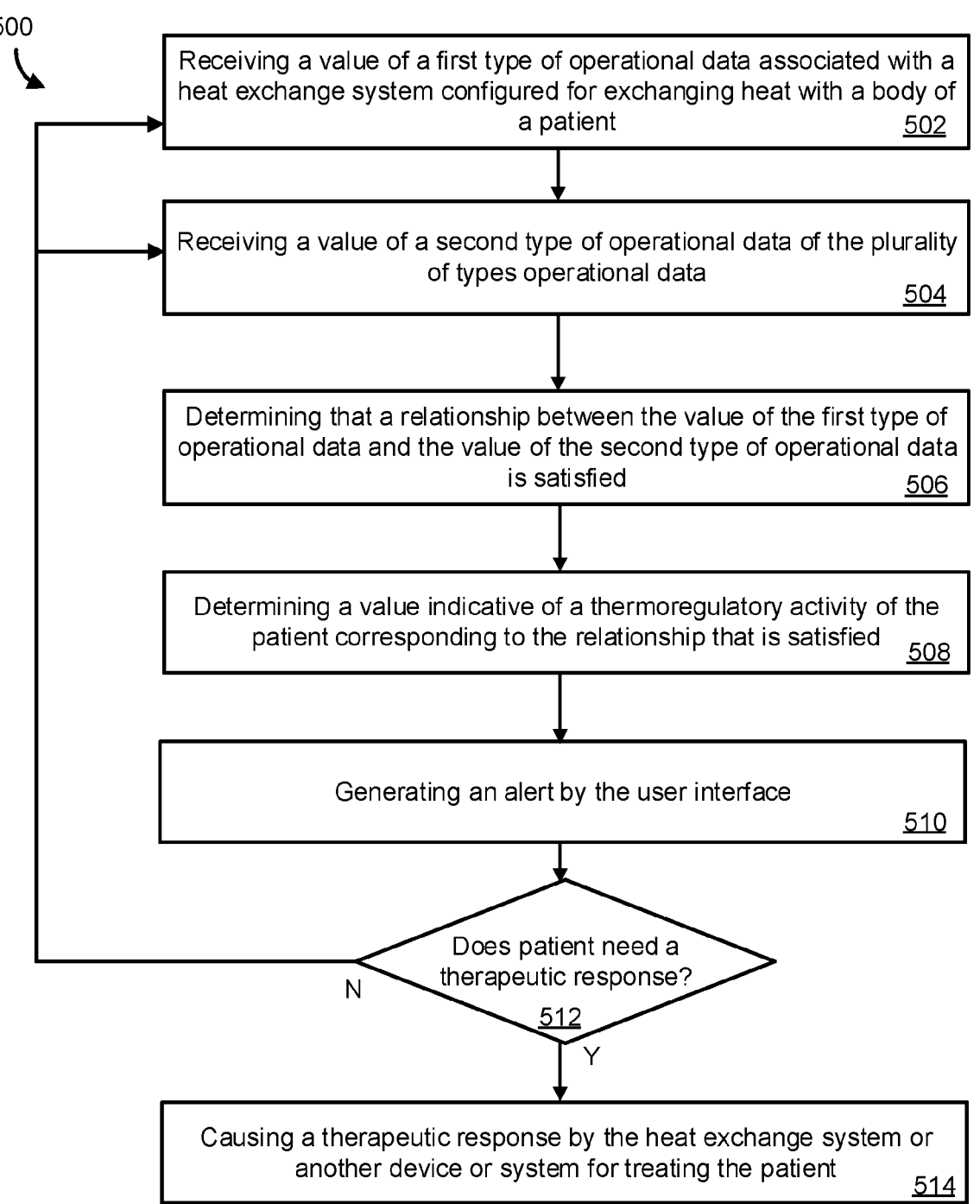

500

Receiving a value of a first type of operational data associated with a heat exchange system configured for exchanging heat with a body of a patient     502

Receiving a value of a second type of operational data of the plurality of types operational data     504

Determining that a relationship between the value of the first type of operational data and the value of the second type of operational data is satisfied     506

Determining a value indicative of a thermoregulatory activity of the patient corresponding to the relationship that is satisfied     508

Generating an alert by the user interface     510

Does patient need a therapeutic response?     512     N     Y

Causing a therapeutic response by the heat exchange system or another device or system for treating the patient     514

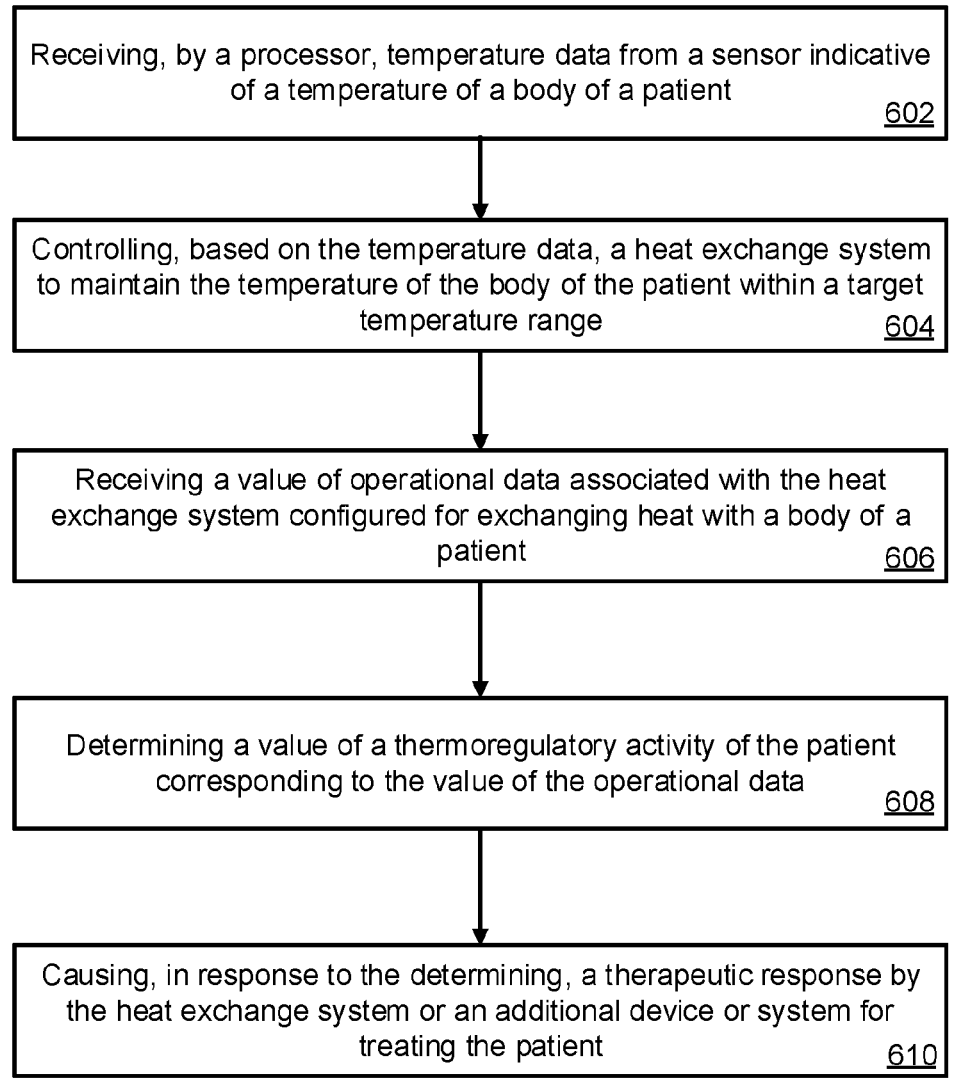

Receiving, by a processor, temperature data from a sensor indicative of a temperature of a body of a patient
602

Controlling, based on the temperature data, a heat exchange system to maintain the temperature of the body of the patient within a target temperature range
604

Receiving a value of operational data associated with the heat exchange system configured for exchanging heat with a body of a patient
606

Determining a value of a thermoregulatory activity of the patient corresponding to the value of the operational data
608

Causing, in response to the determining, a therapeutic response by the heat exchange system or an additional device or system for treating the patient
610

| Controlling, based on temperature data, a heat exchange system to maintain the temperature of the body of the patient within a target temperature range                                                                    802 |

| Receiving, in response to the controlling, operational data representing a flow rate of heat exchange fluid of the heat exchange system                                                                    804 |

| Compare the flow rate of the received operational data to a normal operational range for the working fluid flow rate (e.g., 50mL/min to 300mL/min)                                                                    806 |

| Determine, based on the comparison, a value indicative of a thermoregulatory activity of the patient                                                                    808 |

| Generating an alert by the user interface                                                                    810 |

Does patient need a therapeutic response?          812

N

Y

| Causing a therapeutic response by the heat exchange system or another device or system for treating the patient                                                                    814 |

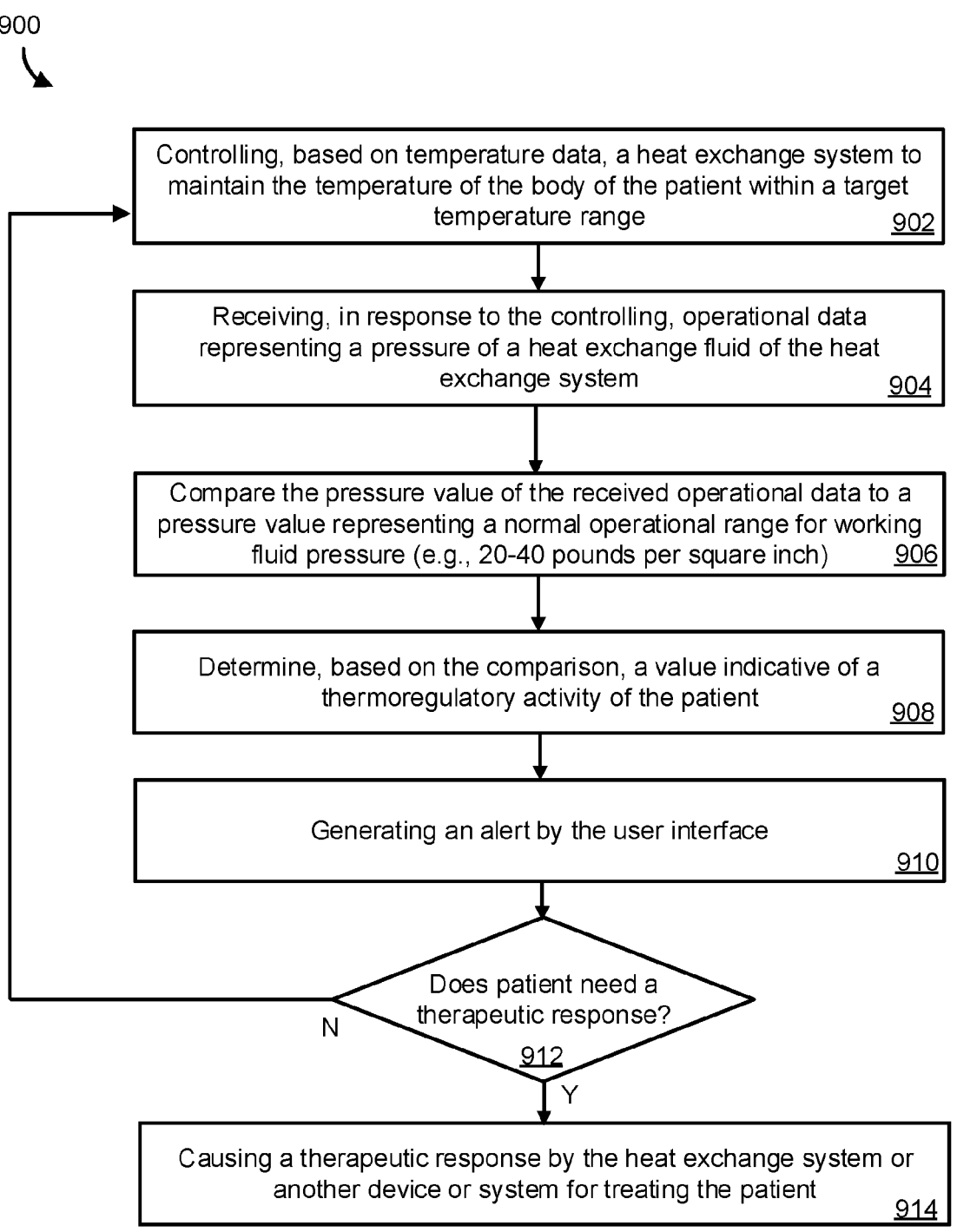

Controlling, based on temperature data, a heat exchange system to maintain the temperature of the body of the patient within a target temperature range 902

Receiving, in response to the controlling, operational data representing a pressure of a heat exchange fluid of the heat exchange system 904

Compare the pressure value of the received operational data to a pressure value representing a normal operational range for working fluid pressure (e.g., 20-40 pounds per square inch) 906

Determine, based on the comparison, a value indicative of a thermoregulatory activity of the patient 908

Generating an alert by the user interface 910

Does patient need a therapeutic response? 912

N

Y

Causing a therapeutic response by the heat exchange system or another device or system for treating the patient 914

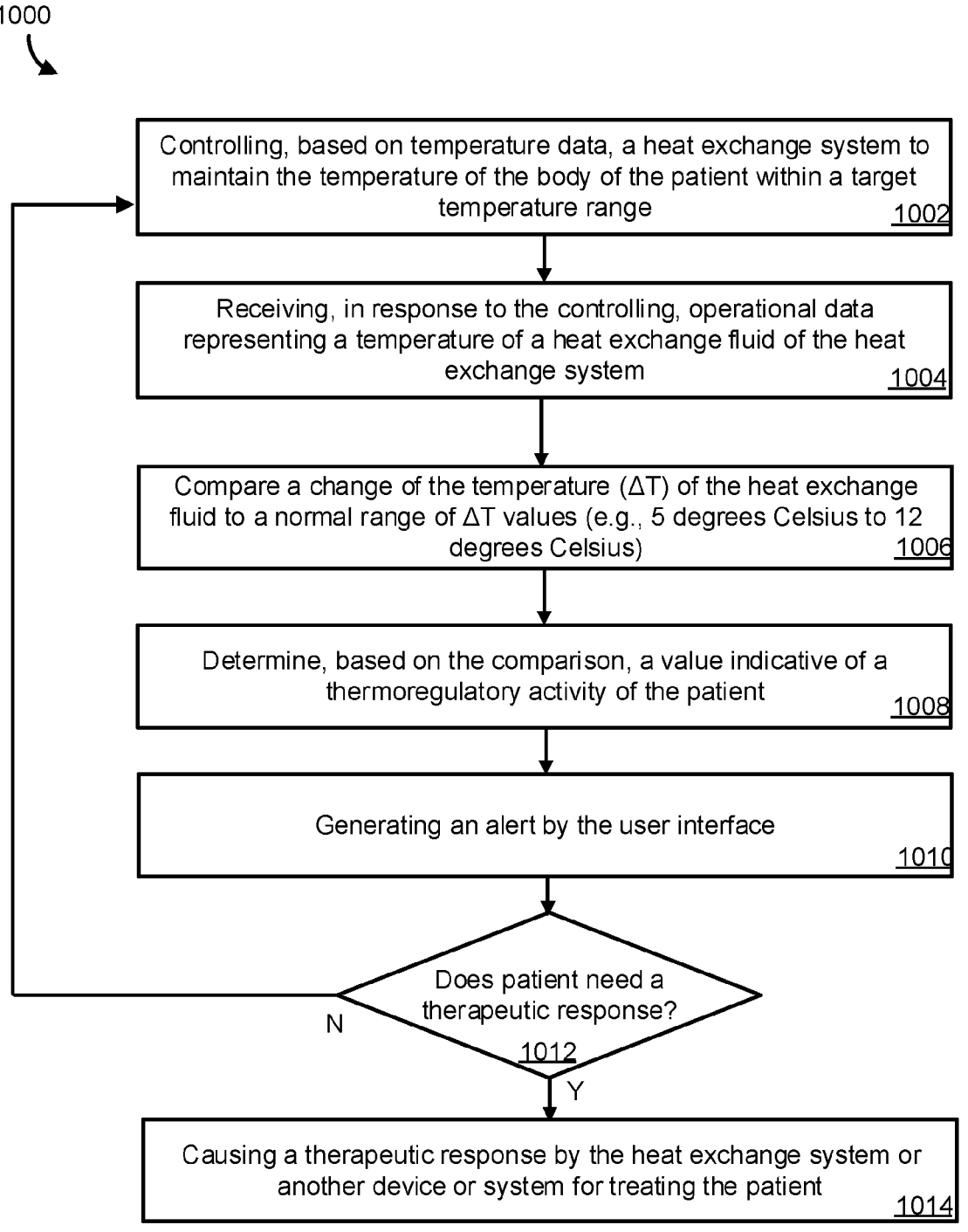

Controlling, based on temperature data, a heat exchange system to maintain the temperature of the body of the patient within a target temperature range                                                                1002

Receiving, in response to the controlling, operational data representing a temperature of a heat exchange fluid of the heat exchange system                                                                1004

Compare a change of the temperature (ΔT) of the heat exchange fluid to a normal range of ΔT values (e.g., 5 degrees Celsius to 12 degrees Celsius)                                                                1006

Determine, based on the comparison, a value indicative of a thermoregulatory activity of the patient                                                                1008

Generating an alert by the user interface                                                                1010

Does patient need a therapeutic response?                                                                1012

N

Y

Causing a therapeutic response by the heat exchange system or another device or system for treating the patient                                                                1014

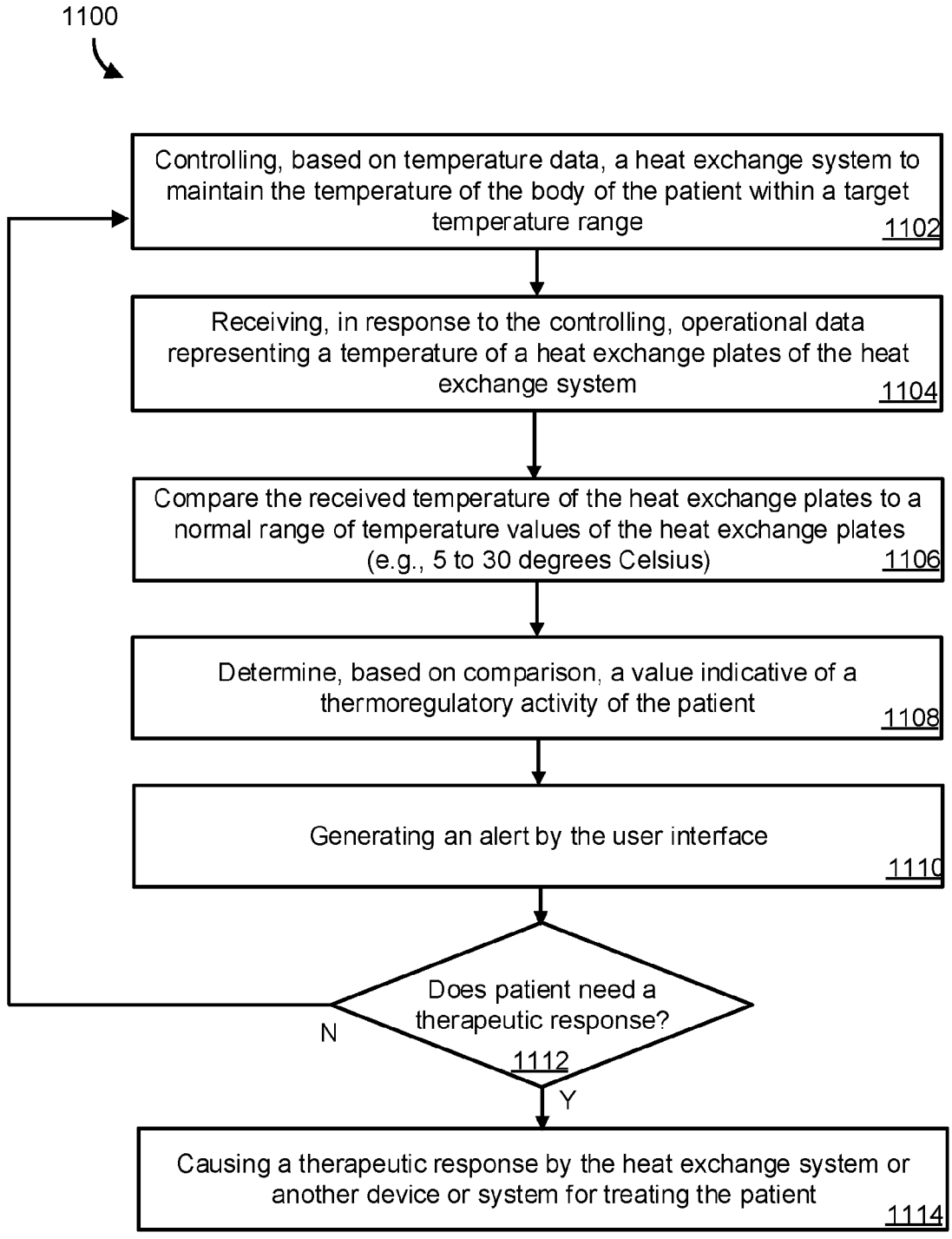

Controlling, based on temperature data, a heat exchange system to maintain the temperature of the body of the patient within a target temperature range          1102

Receiving, in response to the controlling, operational data representing a temperature of a heat exchange plates of the heat exchange system          1104

Compare the received temperature of the heat exchange plates to a normal range of temperature values of the heat exchange plates (e.g., 5 to 30 degrees Celsius)          1106

Determine, based on comparison, a value indicative of a thermoregulatory activity of the patient          1108

Generating an alert by the user interface          1110

Does patient need a therapeutic response?          1112

N

Y

Causing a therapeutic response by the heat exchange system or another device or system for treating the patient          1114

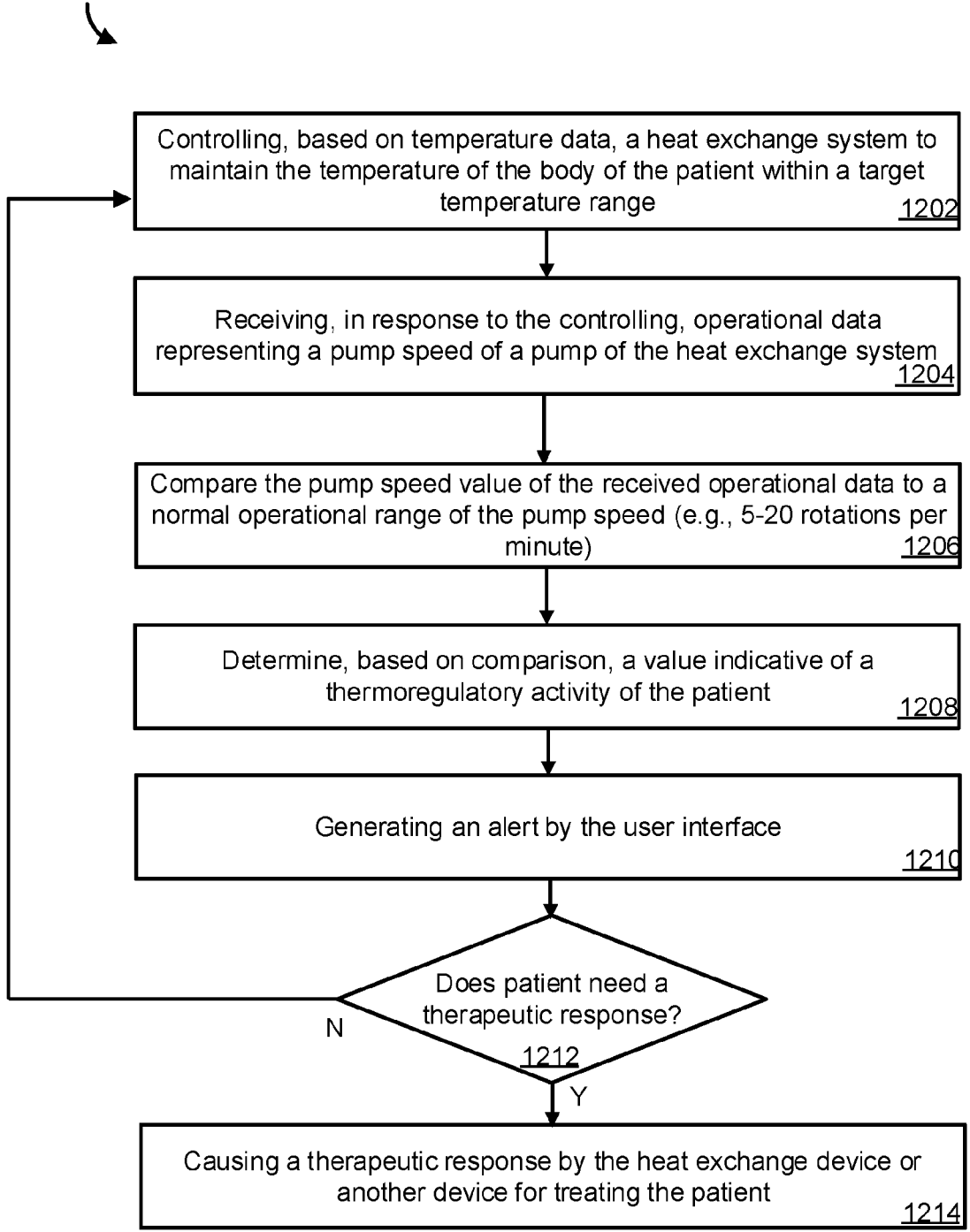

Controlling, based on temperature data, a heat exchange system to maintain the temperature of the body of the patient within a target temperature range          1202

Receiving, in response to the controlling, operational data representing a pump speed of a pump of the heat exchange system          1204

Compare the pump speed value of the received operational data to a normal operational range of the pump speed (e.g., 5-20 rotations per minute)          1206

Determine, based on comparison, a value indicative of a thermoregulatory activity of the patient          1208

Generating an alert by the user interface          1210

Does patient need a therapeutic response?          1212

N

Y

Causing a therapeutic response by the heat exchange device or another device for treating the patient          1214

FIG. 12

DETERMINING A VALUE INDICATIVE OF A THERMOREGULATORY ACTIVITY OF A PATIENT USING A TEMPERATURE MANAGEMENT SYSTEM

CLAIM OF PRIORITY

This application is a national stage application under 35 U.S.C. § 371 of International Application No. PCT/US2021/016590, filed on Feb. 4, 2021, which claims priority under 35 U.S.C. § 119(e) to U.S. Patent Application Ser. No. 62/970,123, filed on Feb. 4, 2020, the entire contents of which are hereby incorporated by reference.

TECHNICAL FIELD

The present disclosure relates generally to the fields of medicine and engineering and more particularly to devices, systems and methods for controlling a patient's body temperature.

BACKGROUND

In various clinical situations, it is desirable to warm, cool or otherwise control the body temperature of a subject. For example, hypothermia can be induced in humans and some animals for the purpose of protecting various organs and tissues (e.g., heart, brain, kidneys) against the effects of ischemic, anoxic or toxic insult. For example, animal studies and/or clinical trials suggest that mild hypothermia can have neuroprotective and/or cardioprotective effects in animals or humans who suffer from ischemic cardiac events (e.g., myocardial infract, acute coronary syndromes, etc.), post-anoxic coma after cardiopulmonary resuscitation, traumatic brain injury, stroke, subarachnoid hemorrhage, fever and neurological injury.

One method for inducing hypothermia is by intravascular or endovascular temperature management wherein a heat exchange catheter is inserted into a blood vessel and a thermal exchange fluid is circulated through a heat exchanger positioned on the portion of the catheter that is inserted in the blood vessel. As the thermal exchange fluid circulates through the catheter's heat exchanger, it exchanges heat with blood flowing past the heat exchange in the blood vessel. Such technique can be used to cool the subject's flowing blood thereby resulting in a lowering of the subject's core body temperature to some desired target temperature. Endovascular temperature management is also capable of warming the body and/or of controlling body temperature to maintain a monitored body temperature at some selected temperature. If a controlled rate of re-warming or re-cooling from the selected target temperature is desired, that too can be accomplished by carefully controlling the amount of heat added or removed from the body and thereby controlling the temperature change of the patient.

SUMMARY

This document describes a temperature management system configured to control a temperature of a patient's body using a heat exchange system. The heat exchange system is configured to determine a value indicative of a thermoregulatory activity of the patient by monitoring how a heat exchange device (such as a catheter, pad, etc.) is operating to control the temperature of the patient's body.

The implementations described herein can provide one or more advantages. The temperature management system can determine a value indicative of thermoregulatory activity, which is indicative of problems with a patient's thermoregulatory response. These problems may be masked when the patient is being treated by the temperature management system to control the body temperature of the patient. Problems with a patient's thermoregulatory response may indicate that the patient has neurological damage which should be treated by other means. A value indicative of the patient's thermoregulatory activity may indicate that the patient has an infection or is experiencing a febrile state, which may require additional temperature control and/or other therapeutic responses besides temperature control. The determined values, which are indicative of thermoregulatory activity of a patient, may be used by the system to control or modify heating or cooling treatment of the patient. The determined values, which are indicative of thermoregulatory activity of a patient, may be used by the system or caregiver to assess a patient's health and to treat a patient. For example, the temperature management system may generate an alert that informs a health care provider locally or in a remote location of a value indicative of a patient's thermoregulatory activity and/or send the alert to another device to quickly induce a response by the health care provider.

The implementations described herein can include one or more of the following embodiments. In particular, it will be appreciated that the implementations described in the passages below may be provided in combination with any of the aspects described below.

In an aspect, there is provided a temperature management system for controlling a temperature of a body of a patient and for determining a value indicative of a thermoregulatory activity of the patient includes a heat exchange system including a heat exchange device and an extracorporeal control console, the heat exchange system configured to exchange heat with a body of a patient and to record operational data while controlling the temperature of the body of the patient. The system may include a sensor configured to measure temperature data indicative of a temperature of the body of the patient. The system may include a user interface, which may be configured to receive user input and may be configured to emit at least one of a visual alert and audible alert. The system includes a processor, a memory storing instructions, and associated circuitry communicatively coupled to the sensor. The processor is configured to: receive the temperature data from the sensor indicative of the temperature of the body of the patient; control, based on the temperature data, the heat exchange system to maintain the temperature of the body of the patient within a target temperature range; receive, in response to the controlling, the operational data; determine, based on the temperature data and the operational data, a value indicative of a thermoregulatory activity of the patient; and may generate, based on the value, an alert indicating the thermoregulatory activity of the patient. The alert may be generated, based on the value, through the user interface indicating the thermoregulatory activity of the patient. The processor may be configured to, in response to determining the value, cause a therapeutic response by the heat exchange system or an additional device or system for treating the thermoregulatory activity of the patient. The processor may be configured to both generate an alert and cause a therapeutic response.

In some implementations, the alert comprises a score, the score being indicative of a patient presenting an underlying hyperthermic state or hypothermic state. In some implementations, the alert comprises a score, the score being indicative of the patient having a damaged or compromised endogenous thermoregulatory mechanism. In some implementations, the processor is configured for determining an effectiveness of an endogenous thermoregulatory mechanism of the patient in changing the temperature of the body of the patient. In some implementations, the value represents cooling power required to change the temperature of the body of the patient a number of degrees over a predefined time interval, the number of degrees being indicative of an effectiveness of an endogenous thermoregulatory mechanism of the patient.

In some implementations, the operational data comprises one or more types of operational data selected from: flow rate of heat exchange fluid circulating through the heat exchange system, a pressure of the heat exchange system, a pressure of heat exchange fluid circulating through the heat exchange system, a temperature of heat exchange fluid circulating through the heat exchange system, a temperature of heat exchange plates in the heat exchange system, a power consumption of the heat exchange system and a pump speed of a pump of the heat exchange system.

In some implementations, the heat exchange device comprises an intravascular heat exchange catheter or a heat exchange surface pad for exchanging heat with the patient.

In some implementations, the processor is configured, in response to determining the value indicative of the thermoregulatory activity, to cause a therapeutic response by the heat exchange system or another device or system for treating the thermoregulatory activity of the patient. In some implementations, the system includes a catheter coupled to the sensor, and the sensor is configured to measure a blood temperature of the patient.

In some implementations, the processor is configured to generate the alert indicating the thermoregulatory activity of the patient in response to a rate of change value of the blood temperature exceeding a threshold rate of change value. In some implementations, the processor is configured to determine a mass flow rate based on a change in blood temperature over time. In some implementations, the processor is configured to determine a cardiac output value of the patient based on the mass flow rate. In some implementations, generating the alert indicating the thermoregulatory activity of the patient is based on the cardiac output value of the patient exceeding a threshold cardiac output value.

In some implementations, the operational data comprise a power consumption value of the heat exchange system. In some implementations, the processor is configured to determine the power consumption value associated with controlling the heat exchange system to maintain the temperature of the body of the patient within the target temperature range, and where the alert indicating the thermoregulatory activity of the patient is generated in response to the power consumption value exceeding a threshold power consumption value.

In some implementations, the heat exchange system includes a fluid reservoir for storing a cooling fluid. In some implementations, the operational data comprise a fluid reservoir temperature associated with the fluid reservoir of the heat exchange system. The processor may be configured to generate the alert indicating the thermoregulatory activity of the patient based on the fluid reservoir temperature.

In some implementations, the processor is configured to transmit the alert indicating the thermoregulatory activity of the patient to a remote device associated with a treatment provider. In some implementations, transmitting the alert indicating the thermoregulatory activity of the patient to the remote device comprises triggering a phone call, text message or email. The remote device may comprise the user interface.

In some implementations, the system includes a display device configured to communicate with the processor, where the alert indicating the thermoregulatory activity of the patient causes a notification to be displayed on the display device.

In some implementations, the processor is further configured to receive training data including a plurality of measurements of a first type of operational data for a plurality of patients; determine, based on the training data, a relationship between the first type of operational data of the heat exchange system and the thermoregulatory activity of the patient; and adjust one or more thresholds associated with the first type of operational data for generating the alert indicating the thermoregulatory activity of the patient based on the relationship. In some implementations, the thermoregulatory activity of the patient comprises at least of a febrile state, an infected state, and a hypothermic state.

In an aspect, a temperature management system for controlling a temperature of a body of a patient and for determining a value indicative of a thermoregulatory activity of the patient includes a heat exchange system including a heat exchange device and an extracorporeal control console. The heat exchange system configured to exchange heat with the body of the patient and to record operational data while controlling the temperature of the body of the patient. The system may include a user interface, which may be configured to receive user input and may be configured to emit at least one of a visual alert and audible alert. The system includes a processor, a memory storing instructions, and associated circuitry communicatively coupled to the heat exchange device, where the processor is configured to: receive a value of a first type of operational data of a plurality of types of the operational data; receive a value of a second type of operational data of the plurality of types of the operational data; determine that a relationship between the value of the first type of the operational data and the value of the second type of the operational data is satisfied; determine a value indicative of a thermoregulatory activity of the patient corresponding to the relationship that is satisfied; and may generate, based on the value, an alert indicating the thermoregulatory activity of the patient. The processor may be configured to generate, based on the value, the alert through the user interface indicating the thermoregulatory activity of the patient. The processor may be configured to, in response to determining the value, cause a therapeutic response by the heat exchange system or an additional device or system for treating the thermoregulatory activity of the patient. The processor may be configured to both generate an alert and cause a therapeutic response.

In some implementations, the first type and the second type of the operational data each comprise of a flow rate of heat exchange fluid circulating through the heat exchange system, a pressure of the heat exchange system, a pressure of heat exchange fluid circulating through the heat exchange system, an ex vivo temperature of the heat exchange system, a temperature within the heat exchange system, a temperature of heat exchange fluid circulating through the heat exchange system, a temperature of heat exchange plates in the heat exchange system, a power consumption of the heat exchange system and a pump speed of a pump of the heat exchange system.

In some implementations, the heat exchange device includes one or both of a catheter and surface pad for exchanging heat with the patient.

In some implementations, the processor is configured, in response to determining the value indicative of the thermoregulatory activity of the patient, to cause a therapeutic response by the heat exchange system or another device or system for treating the thermoregulatory activity of the patient.

In some implementations, the therapeutic response by the heat exchange system or another device or system comprises an automatic injection or infusion of a supplemental fluid. In some implementations, the automatic injection or infusion is an injection or infusion of an anti-shivering medication. In some implementations, the therapeutic response by the heat exchange system comprises raising or lowering a body temperature of the patient.

In some implementations, determining that the relationship between the value of the first type of the operational data and the value of the second type of the operational data is satisfied comprises: determining that the value of the first type of the operational data exceeds a first threshold; and determining that the value of the second type of the operational data exceeds a second threshold. In some implementations, determining that the relationship between the value of the first type of the operational data and the value of the second type of the operational data is satisfied comprises: determining that the value of the first type of the operational data is within a first predetermined value range; and determining that the value of the second type of the operational data is within a second predetermined value range.

In an aspect, there is provided a temperature management system for controlling a temperature of a body of a patient and for determining a value indicative of a thermoregulatory activity of the patient includes a heat exchange system including a heat exchange device and an extracorporeal control console. The heat exchange system may be configured to exchange heat with the body of the patient and to record operational data representing operation of the heat exchange device while controlling the temperature of the body of the patient. The system may include a user interface, which may be configured to receive user input and may be configured to emit at least one of a visual alert and audible alert. The system includes a processor, a memory storing instructions, and associated circuitry communicatively coupled to the heat exchange system. The processor is configured to: receive the operational data; determine a value indicative of a thermoregulatory activity of the patient corresponding to the of the operational data; and may in response to determining the value, cause a therapeutic response by the heat exchange system or an additional device or system for treating the thermoregulatory activity of the patient. The processor may be configured to generate, based on the value, the alert through the user interface indicating the thermoregulatory activity of the patient. The processor may be configured to both generate an alert and cause a therapeutic response.

In some implementations, the operational data includes one or more of a flow rate of heat exchange fluid circulating through the heat exchange system, a pressure of the heat exchange system, a pressure of heat exchange fluid circulating through the heat exchange system, an ex vivo temperature of the heat exchange system, a temperature within the heat exchange system, a temperature of heat exchange fluid circulating through the heat exchange system, a temperature of heat exchange plates in the heat exchange system, a power consumption of the heat exchange system and a pump speed of a pump of the heat exchange system.

In some implementations, the heat exchange device includes one or both of a catheter and a surface pad for exchanging heat with the patient.

In some implementations, the therapeutic response by the heat exchange system or another device or system comprises an automatic injection or infusion of a supplemental fluid. In some implementations, the automatic injection or infusion is an injection or infusion of an anti-shivering medication. In some implementations, the therapeutic response by the heat exchange system comprises raising or lowering a body temperature of the patient.

In an aspect, there is provided a method for controlling a temperature of a body of a patient and for determining a value indicative of a thermoregulatory activity of the patient includes receiving, by a processor, temperature data from a sensor indicative of the temperature of the body of the patient; controlling, by the processor based on the temperature data, a heat exchange system to maintain the temperature of the body of the patient within a target temperature range, the heat exchange system being configured to exchange heat with the body of the patient and to record operational data representing operation of the heat exchange system while controlling the temperature of the body of the patient; receiving, by the processor in response to the controlling, the operational data; determine, based on the temperature data and the operational data, a value indicative of a thermoregulatory activity of the patient; and may comprise generating, by the processor, an alert indicating the thermoregulatory activity of the patient. The method may comprise causing, by the processor in response to determining the value, a therapeutic response by the heat exchange system or an additional device or system for treating the thermoregulatory activity of the patient.

In some implementations, the alert comprises a score, the score being indicative of a patient presenting an underlying hyperthermic state or hypothermic state. In some implementations, the alert comprises a score, the score being indicative of the patient having a damaged or compromised endogenous thermoregulatory mechanism.

In some implementations, the actions include determining an effectiveness of an endogenous thermoregulatory mechanism of the patient in changing the temperature of the body of the patient.

In some implementations, the value represents cooling power required to change the temperature of the body of the patient a number of degrees over a predefined time interval, the number of degrees being indicative of an effectiveness of an endogenous thermoregulatory mechanism of the patient.

In some implementations, the operational data comprise one or more of a flow rate of heat exchange fluid circulating through the heat exchange system, a pressure of the heat exchange system, a pressure of heat exchange fluid circulating through the heat exchange system, an ex vivo temperature of the heat exchange system, a temperature within the heat exchange system, a temperature of heat exchange fluid circulating through the heat exchange system, a temperature of heat exchange plates in the heat exchange system, a power consumption of the heat exchange system and a pump speed of a pump of the heat exchange system.

In some implementations, the heat exchange system includes one or both of a catheter and surface pad for exchanging heat with the patient.

In some implementations, the processor is configured, in response to determining the value indicative of the thermoregulatory activity, to cause a therapeutic response by the heat exchange system or another device or system for treating the thermoregulatory activity of the patient.

In some implementations, a catheter is coupled to the sensor, the sensor is configured to measure a blood temperature of the patient.

In some implementations, the processor is configured to generate the alert indicating the thermoregulatory activity of the patient in response to a rate of change value of the blood temperature exceeding a threshold rate of change value. In some implementations, the processor is configured to determine a mass flow rate based on a change in blood temperature over time. In some implementations, the processor is configured to determine a cardiac output value of the patient based on the mass flow rate. In some implementations, generating the alert indicating the thermoregulatory activity of the patient is based on the cardiac output value of the patient exceeding a threshold cardiac output value.

In some implementations, the operational data comprise a power consumption value of the heat exchange system, where the processor is configured to determine the power consumption value associated with controlling the heat exchange system to maintain the temperature of the body of the patient within the target temperature range. The alert indicating the thermoregulatory activity of the patient may be generated in response to the power consumption value exceeding a threshold power consumption value.

In some implementations, the heat exchange system comprises a fluid reservoir for storing a cooling fluid. The operational data comprise a fluid reservoir temperature associated with the fluid reservoir of the heat exchange system. The processor may be configured to generate the alert indicating the thermoregulatory activity of the patient based on the fluid reservoir temperature.

In some implementations, the processor is configured to transmit the alert indicating the thermoregulatory activity of the patient to a remote device associated with a treatment provider. In some implementations, transmitting the alert indicating the thermoregulatory activity of the patient to the remote device comprises triggering a phone call, text message or email. The remote device may comprise the user interface.

In some implementations, a display device is configured to communicate with the processor. The alert indicating the thermoregulatory activity of the patient may cause a notification to be displayed on the display device.

In some implementations, the actions include receiving, by the processor, training data including a plurality of measurements of a first type of operational data for a plurality of patients; determining, by the processor based on the training data, a relationship between the first type of the operational data of the heat exchange system and the thermoregulatory activity of the patient; and adjusting, by the processor, one or more thresholds associated with the first type of the operational data for generating the alert indicating the thermoregulatory activity of the patient based on the relationship. In some implementations, the thermoregulatory activity of the patient comprises at least of a febrile state, an infected state, and a hypothermic state.

In an aspect, there is provided a method for controlling a temperature of a body of a patient and for determining a value indicative of a thermoregulatory activity of the patient includes receiving, by a processor, a value of a first type of operational data of a plurality of types of operational data associated with a heat exchange system configured for exchanging heat with the body of the patient; receiving, by the processor, a value of a second type of the operational data of the plurality types of the operational data; determining, by the processor, that a relationship between the value of the first type of the operational data and the value of the second type of the operational data is satisfied; determining, by the processor, a value indicative of a thermoregulatory activity of the patient corresponding to the relationship that is satisfied; and may comprise generating an alert indicating the thermoregulatory activity of the patient. The alert may be generated through a user interface. The method may comprise causing, by the processor in response to determining the value, a therapeutic response by the heat exchange system or an additional device or system for treating the thermoregulatory activity of the patient.

In some implementations, the types of operational data comprise two or more of a flow rate of heat exchange fluid circulating through the heat exchange system, a pressure of the heat exchange system, a pressure of heat exchange fluid circulating through the heat exchange system, an ex vivo temperature of the heat exchange system, a temperature within the heat exchange system, a temperature of heat exchange fluid circulating through the heat exchange system, a temperature of heat exchange plates in the heat exchange system, a power consumption of the heat exchange system and a pump speed of a pump of the heat exchange system. The heat exchange system may include one or both of a catheter and a surface pad for exchanging heat with the patient. The processor may be configured, in response to determining the value indicative of the thermoregulatory activity of the patient, to cause a therapeutic response by the heat exchange system or another device or system for treating the thermoregulatory activity of the patient. The therapeutic response by the heat exchange system or another device or system may comprise an automatic injection or infusion of a supplemental fluid. The automatic injection or infusion may be an injection or infusion of an anti-shivering medication. The therapeutic response by the heat exchange system comprises raising or lowering a body temperature of the patient. Determining that the relationship between the value of the first type of the operational data and the value of the second type of the operational data is satisfied may comprise: determining that the value of the first type of the operational data exceeds a first threshold; and determining that the value of the second type of the operational data exceeds a second threshold. Determining that the relationship between the value of the first type of the operational data and the value of the second type of the operational data is satisfied may comprise: determining that the value of the first type of the operational data is within a first predetermined value range; and determining that the value of the second type of the operational data is within a second predetermined value range.

In an aspect, there is provided a method for controlling a temperature of a body of a patient and for determining a value indicative of a thermoregulatory activity of the patient includes receiving, by a processor, operational data associated with a heat exchange system including a heat exchange device and an extracorporeal console, the heat exchange system configured for exchanging heat with the body of the patient while controlling the temperature of the body of the patient; determining, by the processor, a value indicative of a thermoregulatory activity of the patient corresponding to the operational data; and may comprise causing, by the processor in response to determining the value, a therapeutic response by the heat exchange system or an additional device or system for treating the thermoregulatory activity of the patient. The method may comprise generating, by the processor, an alert indicating the thermoregulatory activity of the patient.

In some implementations, the operational data comprises one or more of a flow rate of heat exchange fluid circulating through the heat exchange system, a pressure of the heat exchange system, a pressure of heat exchange fluid circulating through the heat exchange system, an ex vivo temperature of the heat exchange system, a temperature within the heat exchange system, a temperature of heat exchange fluid circulating through the heat exchange system, a temperature of heat exchange plates in the heat exchange system, a power consumption of the heat exchange system and a pump speed of a pump of the heat exchange system. In some implementations, the heat exchange system includes one or both of a catheter and a surface pad for exchanging heat with the patient.

In some implementations, the therapeutic response by the heat exchange system or another device or system comprises an automatic injection or infusion of a supplemental fluid. In some implementations, the automatic injection or infusion is an injection or infusion of an anti-shivering medication. In some implementations, the therapeutic response by the heat exchange system comprises raising or lowering a body temperature of the patient.

In some implementations, a processor is further configured to: determine a rate of change of the temperature of the body of the patient; and determine, based on the rate of change of the temperature of the patient and the operational data, a value indicative of a thermoregulatory activity of the patient. In some implementations, the operational data comprises one or more types of operational data selected from flow rate of heat exchange fluid circulating through the heat exchange system, a pressure of the heat exchange system, a pressure of heat exchange fluid circulating through the heat exchange system, an ex vivo temperature of the heat exchange system, a temperature within the heat exchange system, a temperature of heat exchange fluid circulating through the heat exchange system, a temperature of heat exchange plates in the heat exchange system, a power consumption of the heat exchange system and a pump speed of a pump of the heat exchange system.

In an aspect, there is provided a temperature management system for controlling a temperature of a body of a patient and for determining a value indicative of a thermoregulatory activity of the patient. The system comprises a heat exchange system configured to exchange heat with the body of the patient and to record operational data representing operation of the heat exchange device while controlling the temperature of the body of the patient. The system comprises a processor configured to determine a value indicative of a thermoregulatory activity of the patient based on at least the operational data. The operational data may be data representing operation of the heat exchange device. The operational data may not include a temperature of the body of the patient. An alert may be generated based on the value indicative of the thermoregulatory activity of the patient. A therapeutic response by the heat exchange system or an additional device or system for treating the thermoregulatory activity of the patient may be provided based on the value indicative of the thermoregulatory activity of the patient. The processor may be configured to both generate an alert and cause a therapeutic response. The system may include a memory storing instructions and associated circuitry communicatively coupled to the heat exchange device.

In an aspect, there is provided a method for controlling a temperature of a body of a patient and for determining a value indicative of a thermoregulatory activity of the patient including receiving, by a processor, operational data associated with a heat exchange system configured for exchanging heat with the body of the patient while controlling the temperature of the body of the patient; and determining, by the processor, a value indicative of a thermoregulatory activity of the patient based on at least the operational data.

In an implementation, the processor may be configured to: receive the temperature data from a sensor indicative of the temperature of the body of the patient; control, based on the temperature data, the heat exchange system to maintain the temperature of the body of the patient within a target temperature range; receive, in response to the controlling, the operational data; determine, based on the temperature data and the operational data, a value indicative of a thermoregulatory activity of the patient.

In an implementation, the processor is configured to: receive a value of a first type of operational data of a plurality of types of the operational data; receive a value of a second type of operational data of the plurality of types of the operational data; determine that a relationship between the value of the first type of the operational data and the value of the second type of the operational data is satisfied; determine a value indicative of a thermoregulatory activity of the patient corresponding to the relationship that is satisfied.

In an implementation, the processor is configured to: receive the operational data; determine a value indicative of a thermoregulatory activity of the patient corresponding to the of the operational data.

The operational data may not include the temperature of the body of the patient measured using the sensor.

As with the proceeding implementations, it is contemplated that each of the following implementations may be used in combination with any of the preceding aspects and implementations.

In some implementations, determining the value indicative of the thermoregulatory activity of the patient comprises: comparing a flow rate of heat exchange fluid to a normal range of values for the flow rate of the heat exchange fluid, the normal range being 50 mL/min to 300 mL/min; and determining, based on the comparing, the value indicative of the thermoregulatory activity of the patient. In some implementations, determining the value indicative of the thermoregulatory activity of the patient comprises: comparing a pressure of heat exchange fluid to a normal range of values for the a pressure of the heat exchange fluid, the normal range being 20 pounds per square inch (psi) to 40 psi (about 140 to 275 kPa); and determining, based on the comparing, the value indicative of the thermoregulatory activity of the patient.

In some implementations, determining the value indicative of the thermoregulatory activity of the patient comprises: comparing a change of a temperature ($\Delta T$) of heat exchange fluid to a normal range of values for the $\Delta T$ of the heat exchange fluid, the normal range being 5 degrees Celsius (C.) to 20 degrees C.; and determining, based on the comparing, the value indicative of the thermoregulatory activity of the patient.

In some implementations, determining the value indicative of the thermoregulatory activity of the patient comprises: comparing a temperature of at least one heat exchange plate to a normal range of values for the temperature of at least one heat exchange plate, the normal range being 5 degrees Celsius to 30 degrees Celsius; and determining, based on the comparing, the value indicative of the thermoregulatory activity of the patient.

In some implementations, determining the value indicative of the thermoregulatory activity of the patient comprises: comparing a pump speed value to a normal range of values for the pump speed, the normal range being 5 rotations per minute (rpm) to 20 rpm; and determining, based on the comparing, the value indicative of the thermoregulatory activity of the patient.

In some implementations, a normal operating range of the flow rate of heat exchange fluid circulating through the heat exchange system is between approximately 50 mL/min to 300 mL/min. In some implementations, a normal operating range of the pressure of heat exchange fluid circulating through the heat exchange system is 20 pounds per square inch (psi) to 40 psi (about 140 to 275 kPa). In some implementations, a normal operating range of the temperature of heat exchange fluid circulating through the heat exchange system is 5 degrees Celsius (C.) to 20 degrees C. In some implementations, a normal operating range of the temperature of heat exchange plates in the heat exchange system is 5 degrees C. to 30 degrees C. In some implementations, a normal operating range of the pump speed of a pump of the heat exchange system is 5 rotations per minute (rpm) to 20 rpm.

In some implementations, determining the value indicative of the thermoregulatory activity of the patient comprises: receiving, at machine learning logic, two or more types of the operational data; and applying the machine learning logic to the two or more types of the operational data.

In some implementations, determining the value indicative of the thermoregulatory activity of the patient comprises: receiving operational data representing flow rate of a heat exchange fluid; receiving operational data representing a change in temperature ($\Delta T$) of the heat exchange fluid or representing a temperature of heat exchange plates or both; and determining, based on the flow rate and the $\Delta T$ of the heat exchange fluid or the temperature of heat exchange plates or both, the value indicative of the thermoregulatory activity of the patient.

In some implementations, determining the value indicative of the thermoregulatory activity of the patient comprises: receiving operational data representing fluid pressure of a heat exchange fluid; receiving operational data representing a change in temperature ($\Delta T$) of the heat exchange fluid or representing a temperature of heat exchange plates or both; and determining, based on the fluid pressure and the $\Delta T$ of the heat exchange fluid or the temperature of heat exchange plates or both, the value indicative of the thermoregulatory activity of the patient.

In some implementations, determining the value indicative of the thermoregulatory activity of the patient comprises: receiving operational data representing pump speed of the heat exchange system; receiving operational data representing a change in temperature ($\Delta T$) of a heat exchange fluid or representing a temperature of heat exchange plates or both; and determining, based on the pump speed of the heat exchange system and the $\Delta T$ of the heat exchange fluid or the temperature of heat exchange plates or both, the value indicative of the thermoregulatory activity of the patient.

According to an aspect, there is provided computer program code comprising instructions configured to cause a processor to perform any method disclosed herein. The computer program code may be stored on a non-transitory computer readable medium.

The details of one or more embodiments are set forth in the accompanying drawings and the description below. Other features and advantages will be apparent from the description and drawings, and from the claims.

BRIEF DESCRIPTION OF THE DRAWINGS

FIG. 4 shows a flow diagram including an example process for determining a value indicative of a thermoregulatory activity of a patient using data describing operation of a heat exchange system such as the system of FIGS. 1-3.

FIG. 5 shows a flow diagram including an example process for determining a value indicative of a thermoregulatory activity of a patient using data describing the operation of the heat exchange system such as the system of FIGS. 1-3.

FIG. 6 shows a flow diagram including an example process for determining a value indicative of a thermoregulatory activity of a patient using data describing the operation of the heat exchange system such as the system of FIGS. 1-3.

FIGS. 8-12 show flow diagrams each including an example process for determining a value indicative of a thermoregulatory activity of a patient using data describing the operation of the heat exchange system such as the system of FIGS. 1-3.

DETAILED DESCRIPTION

Figure 1:
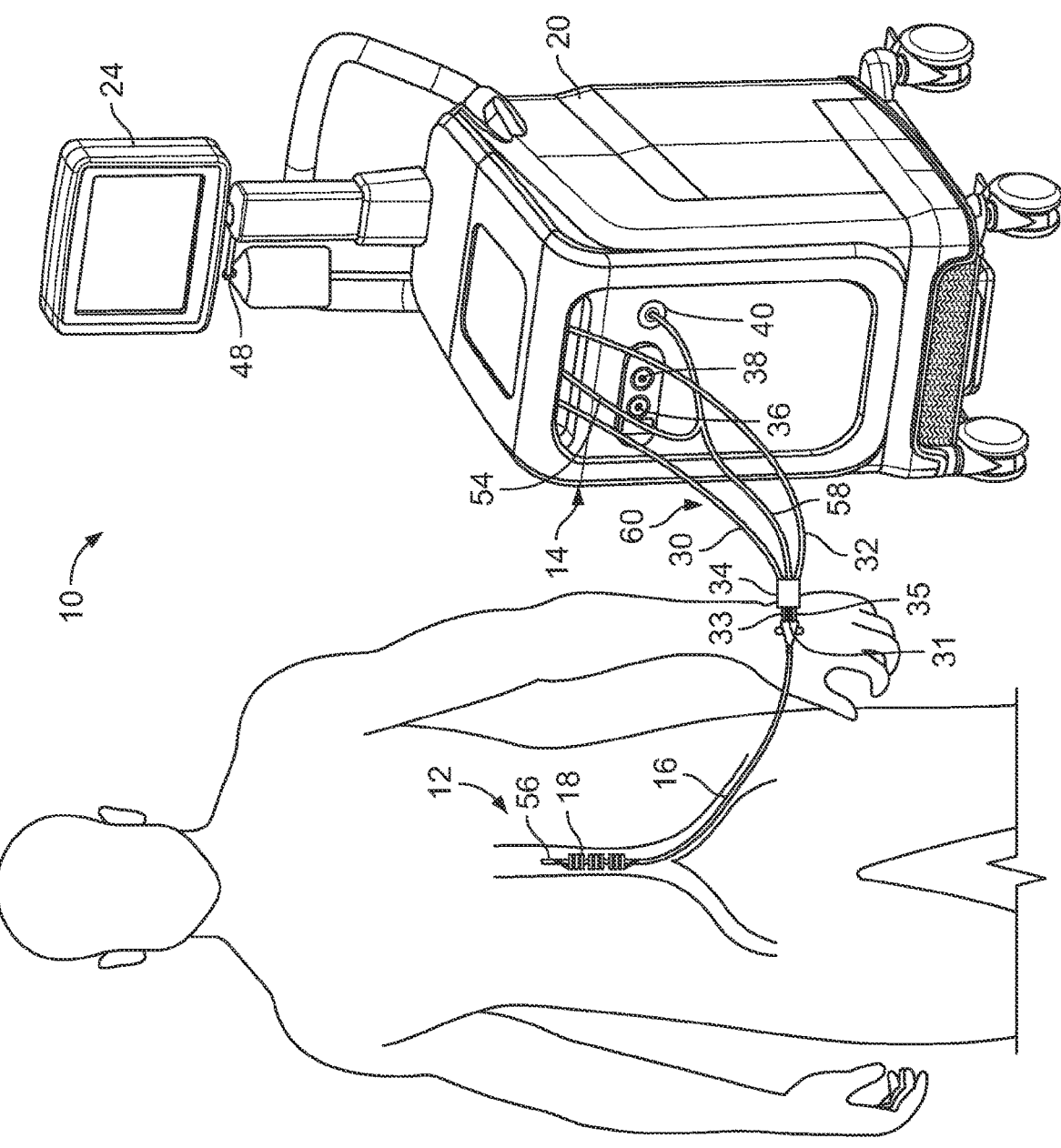
FIG. 1 shows one embodiment of a temperature management system.

This document describes a temperature management system configured to control a temperature of a patient's body using a heat exchange system. The heat exchange system includes a heat exchange device, e.g., an intravascular heat exchange catheter or a heat exchanger applied to the surface of a patient, such as a heat exchange pad. The heat exchange system includes an extracorporeal control console, as subsequently described. The temperature management system is configured to determine a value indicative of the thermoregulatory activity of the patient by monitoring how the heat exchange system is operating to control the temperature of the patient's body. Generally, a system or a health care provider can rely on the temperature of the patient's body as an important vital sign used in assessing a patient's health. Because the thermoregulatory activity or response of a patient is masked by a heat exchange system, which acts to artificially raise, lower or maintain a patient's body temperature, a patient's temperature reading by itself may not be a reliable parameter for assessing the patient's health.

A system for controlling a temperature of a body of a patient may include a processor configured to receive operational data describing operation of the heat exchange system, e.g., via one or more sensors associated with a heat exchange device of the system, and to determine a value indicative of the thermoregulatory activity of the patient. The processor may receive temperature data indicative of the temperature of the body of the patient and may use the temperature data and/or the device operational data to determine a value indicative of the thermoregulatory activity of the patient. The value indicative of the thermoregulatory activity of the patient can provide further context or insight regarding how the patient's body temperature is being changed by the heat exchange system. The value indicative of the thermoregulatory activity of the patient alerts the system or caregiver to the state of the patient and is a factor used by the system or caregiver to assess the patient's health. This determined value may provide predictive information regarding an adverse health condition experienced by the patient that is being masked by the heat exchange system, such as an infection or a thermoregulatory disorder. For example, the value determined by the temperature management system can be indicative of whether or to what degree the patient's thermoregulatory response is resisting temperature control by the temperature management system by attempting to raise or lower body temperature from this desired control. If the patient has an adverse health condition, the patient's body may resist changes in body temperature by the heat exchange system more or less than expected. As a result, the heat exchange system may require more resources (e.g., more power) or operate differently (e.g., at a higher pressure or flow rate) than expected for a healthy patient. In some implementations, the value indicative of thermoregulatory activity may indicate a normal thermoregulatory response by the patient (e.g., a "nominal" health condition), a febrile state, an infected state, a hypothermic state, a hyperthermic state or some combination thereof.

Generally, the temperature management system is configured to measure a value of operational data of the heat exchange system to determine how the heat exchange device is controlling the body temperature of the patient. Operational data can include any data that describes how the heat exchange system is operating. Examples of operational data are subsequently described in relation to the figures.

The temperature management system is configured to determine, based on the operational data, how hard the heat exchange system is working or how much effort the heat exchange system is exerting to maintain a patient's body temperature at a given value. The temperature management system is configured to determine a value indicative of the thermoregulatory activity of the patient by analyzing the values of operational data of the heat exchange system. The values of the operational data provide insight regarding how the heat exchange system is operating. The operation of the heat exchange system, including the heat exchange device of the heat exchange system, provides an indication of the patient's thermoregulatory activity. For example, if the heat exchange device is delivering a high level of cooling power to maintain the patient at normothermia, the temperature management system may determine a high value indicative of the patient's thermoregulatory activity. In this case, the high thermoregulatory activity value, which is associated with a high level of cooling power being delivered to the patient may be indicative of a febrile state (e.g., the patient would have a raised body temperature if the heat exchange device were not cooling the patient's body). While this specific example is provided here as a general illustrative example, many different examples of operational data of the heat exchange system and examples of associated thermoregulatory activity of the patient are subsequently described in further detail with respect to the figures.

The determined value, which is indicative of the thermoregulatory activity of the patient, is predictive of the patient's health. For example, if a patient is febrile, he or she might have high thermoregulatory activity, as described supra. In another example, if the patient has experienced an injury to a thermoregulatory center such as the brain (e.g., after suffering a cardiac arrest), the thermoregulatory activity might be low such that the patient cannot resist temperature management by the heat exchange system. Thermoregulatory activity or capability may correlate to a degree of injury or compromise to a thermoregulatory center/brain or the neural pathways involved.

FIG. 1 shows a temperature management system in operation to control a body temperature of a human patient according to one embodiment of the present disclosure. The temperature management system can include the heat exchange system 10. A user interface, processing device, sensor, and other components of the temperature management system may be included in the heat exchange system 10. This heat exchange system 10 generally comprises a heat exchange catheter 12, an extracorporeal control console 14, a tubing/cassette/sensor module assembly 60 or cassette assembly which facilitates connection of the catheter 12 to the control console 14, and a temperature sensor 56. In some implementations, the catheter 12, tubing/cassette/sensor module assembly 60 or cassette assembly and temperature sensor 56 may be disposable items intended for a single use, while the control console 14 may be a non-disposable device intended for multiple uses.

In the embodiment shown, the intravascular heat exchange catheter 12 comprises an elongate catheter body 16 and a heat exchanger 18 positioned on a distal portion of the catheter body 16. Inflow and outflow lumens (not shown) are present within the catheter body 16 to facilitate circulation of a thermal exchange fluid (e.g., sterile 0.9% sodium chloride solution or other suitable thermal exchange fluid) through the heat exchanger 18. Optionally, the catheter shaft 16 may also include a working lumen (not shown) which extends through the catheter body 16 and terminates distally at an opening in the distal end of the catheter body 16. Such working lumen may serve as a guidewire lumen to facilitate insertion and position of the catheter 12 and/or may be used after insertion of the catheter 12 for delivery of fluids, medicaments or other devices. For example, as shown in FIG. 1, in some embodiments, the temperature sensor 56 may be inserted through the working lumen of the catheter and advanced out of the distal end opening to a location beyond the distal end of the catheter body 16. Alternatively, in other embodiments, the temperature sensor 56 may be positioned at various other locations on or in the subject's body to sense the desired body temperature(s). Various heat exchange catheters may be used in the embodiments described herein.

Non-limiting examples of other heat exchange catheters and related apparatus that may be used are described in U.S. Pat. No. 9,492,633, titled Heat exchange catheter and their methods of manufacture and use and issued on Nov. 15, 2016, and U.S. Application Pub. No. 2013/0090708, titled Endovascular Cooling Catheter System Which Employs Phase-Changing Heat Exchange Media and filed on Sep. 28, 2012, U.S. Pat. No. 9,662,243, titled Heat Exchange Catheters with Bi-Directional Fluid Flow and Their Methods of Manufacture and Use and issued on May 30, 2017, U.S. Pat. No. 10,045,881, titled Patient Temperature Control Catheter with Helical Heat Exchange Paths and issued on Aug. 14, 2018, U.S. Pat. No. 9,314,370 titled Self-Centering Patient Temperature Control Catheter and issued on Apr. 19, 2016, U.S. Pat. No. 9,241,827 titled Intravascular Heat Exchange Catheter with Multiple Spaced Apart Discrete Coolant Loops and issued on Jan. 26, 2016, U.S. Pat. No. 9,717,625 titled Intravascular Heat Exchange Catheter with Non-Round Coiled Coolant Path and issued on Aug. 1, 2017, U.S. Pat. No. 9,433,526 titled Intravascular Heat Exchange Catheter With Rib Cage-Like Coolant Path and issued on Sep. 6, 2016, 2018/0185193, titled High Efficiency Heat Exchange Catheters For Control Of Patient Body Temperature and filed on Dec. 30, 2016, U.S. Pat. App. 2018/018519, filed on Dec. 30, 2016, titled Fluid-Circulating Catheters Useable for Endovascular Heat Exchange, and 2018/0207024, titled Managing Patient Body Temperature Using Endovascular Heat Exchange In Combination With Body Surface Heat Exchange and filed on Jan. 23, 2017, the entire disclosure of each such patent and application being expressly incorporated herein by reference. Other examples of catheters that may be used in this invention include those commercially available from ZOLL Circulation, Inc., San Jose, Calif., such as the Cool Line® Catheter, Icy® Catheter, Quattro® Catheter Solex 7® Catheter. Additionally, incorporated herein by reference is the entire disclosure of U.S. Pat. Application Ser. No. 2018/0325725 entitled Advanced Systems and Methods for Patient Body Temperature Control, filed on May 12, 2017.

The extracorporeal control console 14 generally comprises a main housing 20 and a console head 24. The main housing 20 contains various apparatus and circuitry for warming/cooling thermal exchange fluid to controlled temperature(s) and for pumping such warmed or cooled thermal exchange fluid through the catheter 18 to effectively modify and/or control the subject's body temperature. The console head 24 comprises a display device or user interface, such as a touch screen system, whereby certain information may be input by, and certain information may be displayed to, users of the system 10. On the housing 20 there are provided a first connection port 40 for connection of a temperature sensor 56 that is inserted through the heat exchange catheter 12 as shown in FIG. 1 as well as other connection ports 36, 38 for connection of additional or alternative types of temperature sensors and/or other apparatus.

Figure 3:
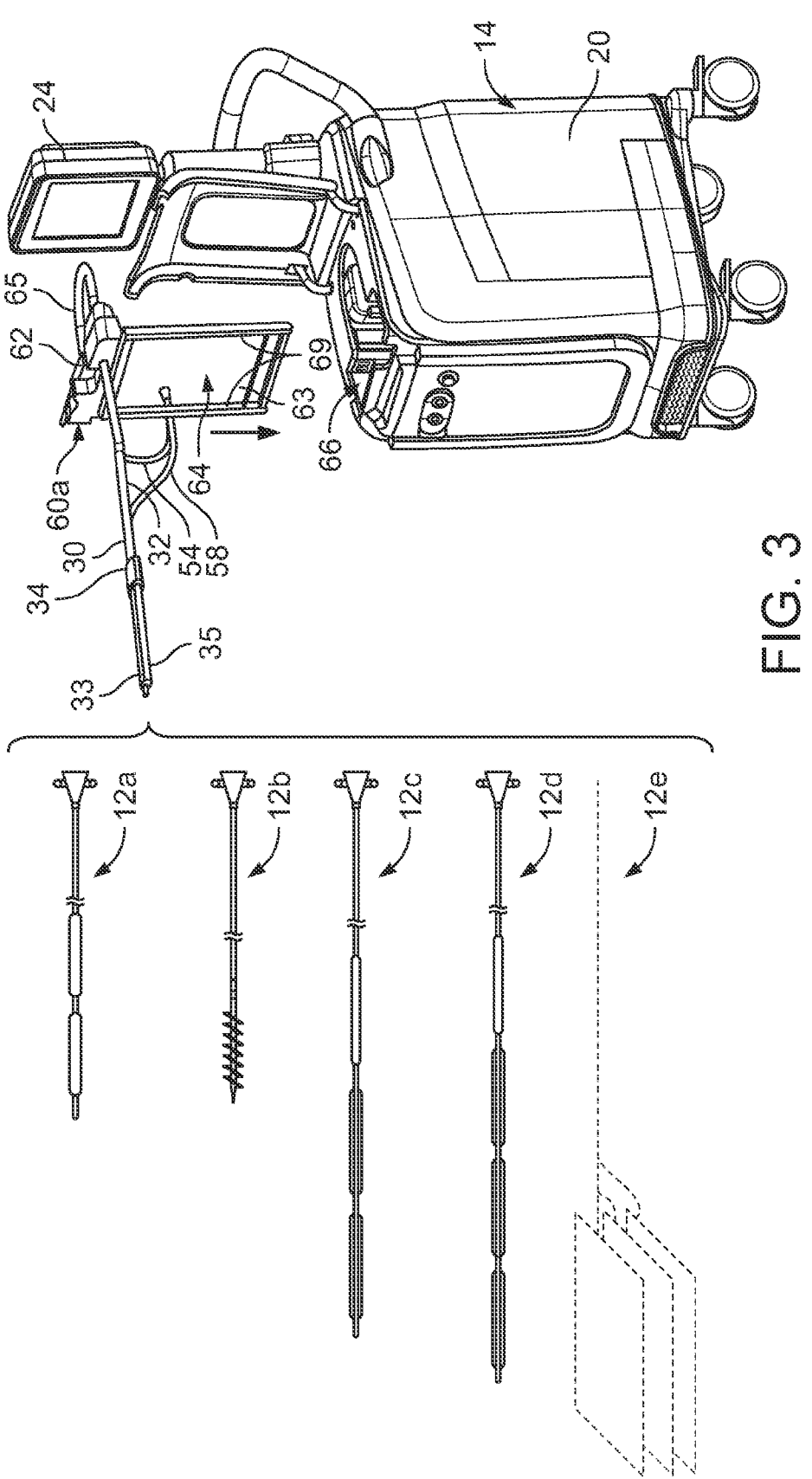
FIG. 3 shows the system of FIGS. 1-2B in combination with partial views of a plurality of heat exchange catheters, any of which may be connected to and used in conjunction with the system.

The tubing/cassette/sensor module assembly 60 or cassette assembly, an example of which is seen in further detail in FIG. 3, generally comprises a sensor module 34, an inflow conduit 32, inflow connector 33, outflow conduit 30, outflow connector 35, temperature lead 58, temperature lead connector 31, pressure lead 54, cassette 64, cassette housing 62 and peristaltic pump tubing 65. In certain embodiments, the pump tubing may be made of materials suitable for continuous or intermittent use over a desired period of time, e.g., suitable for use over a period of time from 20 minutes to 12 hours or 1 hour to 7 days or longer. Examples of such material include Elastollan®, Norprene® and other similar materials.

The cassette housing 62 is attached to a frame 69 which supports the side edges of the expandable vessel or bag 63. In certain embodiments, the vessel or bag may include one or more sides having a thickness suitable to prevent tears during use or manufacture. For example, the thickness may be 0.001 inches-0.005 inches (about 0.025-0.13 mm). In certain embodiments the thickness may be about 0.002 inches (about 0.05 mm). A lower edge 63a of the expandable vessel or bag is sealed and may include a support.

Figures 2A, 2B:
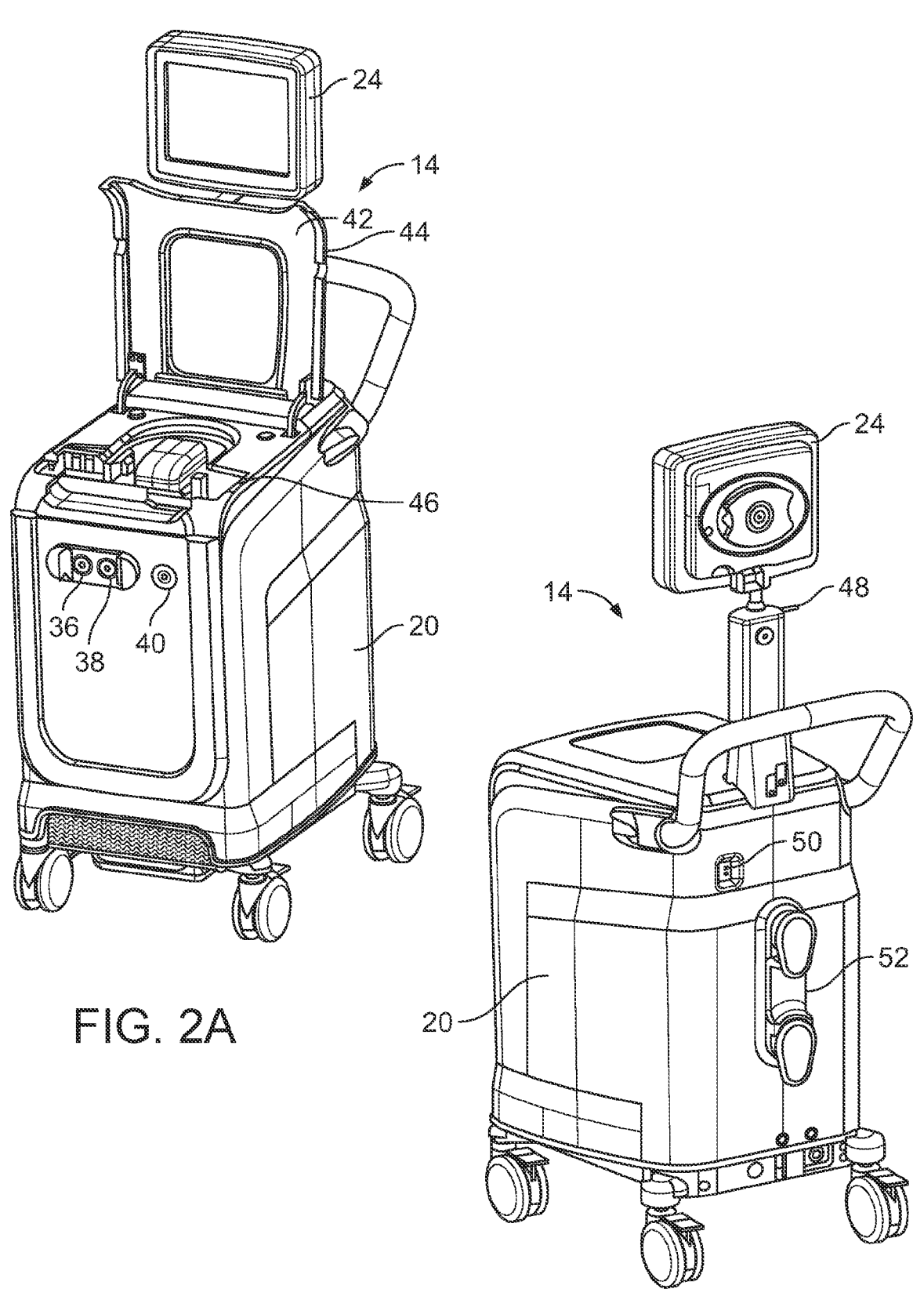
FIG. 2A is a left/front perspective view of the control console with its access cover in an open position.
FIG. 2B is a left/rear perspective view of the control console.

FIGS. 2A-2B show further detail of the components within the housing 20 and the manner in which the tubing/cassette/sensor module assembly 60 or cassette assembly is inserted in and connected to the control console 14. The control console 14 has an openable/closable access cover 42 which, when opened, permits insertion of the cassette 64 into a cassette receiving space 66 as well as other connection of the tubing/cassette/sensor module assembly 60 or cassette assembly to other components of the system described below. A magnet 44 on the access cover 42 interacts with a magnetic sensor 46 to emit signal(s) indicating whether the access cover 42 is opened or closed. Other sensors and detection mechanisms known to persons having skill in the art may be utilized as well. The processor located in the housing 20 may be programmed to halt running of certain components of the system when the access cover 44 is opened. On the rear of the housing 20, there is provided a power switch 50 and a power cord holder 52. A bracket 48 is provided on an upstanding portion of the housing which supports the console head 24 for hanging a bag or container of fluid.

Returning to FIG. 1, a particular tubing/cassette/sensor module assembly 60 (a "first" cassette assembly) may be useable or approved for use with only one type of body heat exchanger. In such embodiments, the sensing module 34 may be encoded with information that is specific not only to the first cassette but which also includes or causes the processor to use algorithms and/or operational settings/variables that are specific to the particular body heat exchanger type, e.g., catheter type or body surface heat exchanger (e.g., pad or garment) type that is useable or approved for use with that first cassette assembly 60.

Turning to FIG. 3, the first cassette assembly 60 or another cassette assembly 60a (a "second" cassette assembly) may be useable or approved for use with a plurality of different types of body heat exchangers, such as heat exchange catheters or body surface heat exchangers, e.g., heat exchanging blankets, pads or garments. In such embodiments, the sensing module 34 may be encoded with information that is specific not only to the cassette but which also includes or causes the processor to use algorithms and/or operational settings/variables that are specific to the particular body heat exchanger, e.g., catheter type or body surface heat exchanger (e.g., pad or garment) type that is useable or approved for use with that cassette assembly. The second cassette assembly 60a is alternately connectable to and useable with a plurality of different types of approved heat exchange catheters 12a, 12b, 12c, and 12d, and one or more cooling or heating surface pads 12e. In this particular example, the first approved heat exchange catheter 12a shown in FIG. 3 is commercially available as the Cool Line® Catheter (ZOLL Circulation, Inc., San Jose, Calif.), the second approved heat exchange catheter 12b is commercially available as the Solex 7® Catheter (ZOLL Circulation, Inc., San Jose, Calif.), the third approved heat exchange catheter 12c is commercially available as the Icy® Catheter (ZOLL Circulation, Inc., San Jose, Calif.) and the fourth approved heat exchange catheter 12d is commercially available as the Quattro® Catheter (ZOLL Circulation, Inc., San Jose, Calif.). The cooling pads 12e are available as the ZOLL® STx™ Surface Pad System (ZOLL Circulation, Inc., San Jose, Calif.). Although these different types of catheters may have different types of operational data (e.g., different maximum fluid pressure ratings) they are all approved for use with cassette assembly 60a and the sensing module 34 of cassette assembly 60a may contain encoded information which includes, or which causes the processor to select and use, algorithms and/or operational settings or data that are suitable for any of these heat exchange catheters 12a-12d and the one or more cooling or heating surface pads 12e. Specifically, the encoded information in the sensing module 34 may include the particular algorithms and/or operational settings or data to be used, or alternatively the processor may be pre-programmed with a number of different algorithms and/or operational settings or data and may be further programmed to select and implement, on the basis of the encoded cassette information, the algorithm and/or operational settings or data suitable for the catheter or catheters that are useable or approved for use with the inserted cassette assembly 60 or 60a. For example, in certain embodiments, each of the plurality of approved body heat exchangers, e.g., catheters, may have a recommended pressure limit and a cassette's encoded information may include, or cause the controller to select and use, a control algorithm, operational setting or data that limits the speed of a pump such that heat exchange fluid pressure within the body heat exchanger connected to the cassette will not exceed a maximum pressure limit for that body heat exchanger, irrespective of which of the plurality of body heat exchanger types is connected to the cassette.

A temperature management system with extracorporeal control console 14 and tubing/cassette/sensor module assembly 60 includes one example of a heat exchange system having a processor configured to carry out the processes described herein. ZOLL's Thermogard XP® intravascular temperature management system is another example. In certain implementations, a temperature management system may include a heat exchange catheter or heat exchanger applied to the surface of a patient (e.g., pad or garment), an extracorporeal control console having a processor and a heat exchange bath, a heat exchanger (e.g., a coil) configured to be inserted into the heat exchange bath and to be coupled, via a tubing assembly, to the heat exchange catheter or heat exchanger applied to the surface of a patient, and/or one or more sensors, e.g. a temperature sensor, and such temperature management system may carry out the processes described herein. Other intravascular heat exchange systems and heat exchange systems that provide surface cooling and/or warming may also be configured to carry out the processes described herein. The temperature management systems and/or heat exchange systems described herein may include one or more sensors for detecting operational data as described herein.

FIGS. 4-6 and 8-12 show flow diagrams each including an example process for determining a value indicative of the thermoregulatory activity of a patient using data describing the operation of at least a portion of the temperature management system (e.g. heat exchange system 10 of FIGS. 1-3) and/or temperature data from a sensor indicative of the temperature of the body of the patient. The heat exchange system 10 is configured to control the body temperature of the patient, as previously described. A processor (e.g., a system controller) of the heat exchange system 10 receives values of one or more operational data from one or more sensors of the heat exchange system 10 as the patient's body temperature is controlled by the heat exchange system.

The one or more sensors measure the values of the operational data. The particular sensors included for measuring the operational data values of the heat exchange system 10 can vary depending on the hardware configuration of the heat exchange system 10 and depending on the operational data being measured. For example, the sensors can include one or more temperature sensors (e.g., thermistors), a fluid flow rate sensor or meter, a pressure sensor, an ammeter or other sensor for measuring power consumed by one or more components of the heat exchange system 10, a tachometer or other sensor for measuring pump rpm or pump impeller speed, and so forth for measuring the values of the operational data. Some operational data can be determined indirectly, such as determining cooling power delivered by the heat exchange system by measuring via a temperature sensor a change in working fluid temperature $T_{in}$-$T_{out}$ during operation of the heat exchange system 10.

Values of the operational data indicate how the heat exchange system 10 is operating at a given point in time. These values alone in some implementations and in combination with sensed patient temperature in other implementations, are indicative of a patient's thermoregulatory activity. The heat exchange system 10 may have a first operational state when controlling the temperature of a patient who does not have an anomalous health condition. The first operational state can be represented by one or more types of operational data (e.g., parameters of the operational data) having values that are considered normal (e.g., within nominal ranges or satisfying specified value thresholds) for operation of the heat exchange system 10. If the patient is experiencing an adverse health condition, the heat exchange system 10 can have a second, third, fourth, etc. operational state indicating a change from the typical operation of the heat exchange system for controlling the temperature of the body of the patient when the patient does not have an adverse health condition. Thus, the subsequent "anomalous" operational states of the heat exchange system 10 can be represented by one or more types of operational data having values that are considered anomalous, and are indicative of an anomalous thermoregulatory activity of the patient. The patient's thermoregulatory activity provides valuable information that may be used by the system or caregiver to assess the patient's health. The "anomalous" operational states of the heat exchange system 10 indicate that the heat exchange system is compensating for additional load or other factors caused by an adverse health condition of the patient while working as intended to control the patient's body temperature.

The operational data can include any measurable value resulting from operation of the heat exchange system 10. In some implementations, the operational data is agnostic to the particular configuration of the temperature control loop (s) of the heat exchange system 10. For example, a type of the operational data can include a power consumption of the heat exchange system 10, such as a wattage consumed. In some implementations, a type of the operational data can include cooling power delivered by the heat exchange system. In some implementations, the type of the operational data can be specific to the particular hardware configuration of the heat exchange system 10. For example, the type of the operational data can include a bath temperature of a coolant well housing a cooling coil, a working fluid reservoir temperature, a temperature of one or each of cold plate(s) through which refrigerant circulates and between which a heat exchange cassette is inserted to exchange heat between the refrigerant and saline circulating within the cassette, an external temperature of one or more pads, and so forth. Many other examples types of operational data are possible. For example, the operational data can include values representing a flow rate of heat exchange fluid circulating through the heat exchange device, a pressure of heat exchange fluid circulating through the heat exchange device, a temperature of heat exchange fluid circulating through the heat exchange device, a temperature of heat exchange plates in the heat exchange device, a pump speed of a pump of the heat exchange device, or any combination thereof. Heat exchange fluid in the above examples may be saline or other solution.

In order to determine a value indicative of a thermoregulatory activity of the patient, the heat exchange system 10 controls the body temperature of the patient and monitors the values of the system's operational data during treatment. The processor of the heat exchange system 10 receives data from the temperature sensor (e.g., temperature lead 58) and the heat exchange system 10 controls the body temperature of the patient based on the sensed temperature as described in relation to FIGS. 1-3. For example, if the patient's body temperature exceeds a threshold value, the heat exchange system 10 takes corrective action to lower the patient's body temperature below the threshold temperature value. For example, the processor can cause the heat exchange system 10 to decrease a flow rate of working fluid to the catheter by decreasing the working fluid pump speed, or lower the temperature of a working fluid reservoir in order to lower the patient's body temperature. The one or more sensors measuring the operational data of the heat exchange system 10 send data to the processor indicating the values of the operational data. The processor can analyze these values to determine how the operational data have changed in response to the corrective action taken by the heat exchange system 10. For example, to increase the flow rate of the working fluid, the heat exchange system 10 may consume more power.

In one aspect, the heat exchange system 10 controls the heat exchange device responsive to a processor of the temperature management system determining the power consumption value of the heat exchange system. For example, the processor is configured to determine the power consumption value associated with controlling the heat exchange device to maintain the temperature of the body of the patient within a target temperature range. The value can be measured as an instantaneous value, moving average, historical average, or other ways. When the power consumption value satisfies (e.g., exceeds or fails to exceed) a threshold power consumption value, the temperature management system generates an alert representing a value indicative of the thermoregulatory activity of the patient.

As stated previously, the library of types of operational data available to the temperature management system can depend on the hardware configuration of the heat exchange system 10. For example, the heat exchange system 10 can include a fluid reservoir for storing a cooling fluid. The processor can receive a value of operational data including a fluid reservoir temperature associated with the fluid reservoir of the heat exchange device from a fluid reservoir temperature sensor. The fluid reservoir temperature value can be compared to a reference value or to a threshold. The processor can be configured to determine a value indicative of the thermoregulatory activity of the patient based on the fluid reservoir temperature and the temperature data from a sensor indicative of the temperature of the body of the patient. The processor can be configured to generate, based on the determined value, an alert via the user interface of the temperature management system.

The processor may analyze the values of the operational data to determine whether one or more rules have been satisfied. A rule can indicate conditions for the values of the operational data that imply a level of thermoregulatory activity (such as activity indicative of the patient experiencing an adverse health condition) for the patient when the rule is satisfied. A rule (or set of rules) can imply a particular level of thermoregulatory activity for the patient which can be used to assess the health condition of the patient, such as a nominal health condition or a febrile state of the patient. In some implementations, the rules more generally indicate that the patient has a level of thermoregulatory activity indicative of an adverse health condition or that the health condition of the patient is nominal.

The method by which the processor of the temperature management system 10 analyses the operational data to compare to the rules can depend on which operational data are being monitored by the processor and what data is available to the processor. For example, for a first type of operational data, the processor may simply compare the instant value of that operational data to a threshold. More specifically, if the processor is receiving sensor data for monitoring a bath temperature of the heat exchange system 10 for a cooling coil, the processor can compare the instant temperature to a threshold temperature representing a nominal operating temperature of the bath. For example, if the processor is receiving sensor data for monitoring a power consumption of the heat exchange system 10, the processor can take periodic or continuous readings of the power consumption and determine if the current power consumption is higher than a historical average.

The processor can use numerous other techniques for analyzing the operational data from the one or more sensors to determine how the heat exchange system 10 is operating. For example, the temperature management system can determine that a set of values of the operational data match a profile of values. The profile of values can include specific values for each of a plurality of types of operational data (or specified ranges for those values) that together indicate the thermoregulatory activity of the patient (e.g., whether the thermoregulatory response of the patient is anomalous or nominal). In some implementations, the values of the profile are determined by crowdsourcing anonymized patient data to train a machine learning model. In some implementations, the values of the profile are directly specified by users.

In one aspect, the processor of the temperature management system receives training data that includes a plurality of values for a given type of operational data of the heat exchange system 10 for a plurality of patients. The plurality of values are each associated with a known level of thermoregulatory activity or related health condition of patients when the values are measured, which may be determined from patient temperature profile data. The processor determines a relationship between the values of the operational data and the thermoregulatory activity or related health condition of the patient using the training data. The processor sets one or more thresholds associated with the given type of the operational data for generating an alert indicating the thermoregulatory activity or related health condition of the patient based on the determined relationship. For example, the processor can determine from patient data an approximate amount of power generally consumed by the heat exchange system 10 to cool a patient's body temperature by 1° C. If the amount of power consumed for cooling a patient's body is different from the trained value by greater than a threshold difference, the processor may trigger an alert to be sent indicative of the thermoregulatory activity or an adverse health condition. For example, if too little power is consumed, the patient might have neurological damage such that the patient is posing little resistance to a dropping body temperature, and if too much power is consumed, the patient could have an infection and be in a febrile state requiring the system to consume more power to cool the patient. Thus, the alert generated can vary depending on how the measured value compares to the training data. Similar examples can be applied to training the processor for other parameters of the operational data.

The temperature management system can determine that a relationship between two types of the operational data or among a plurality of types of the operational data is satisfied. For example, this can include the value of a first type of the operational data exceeding the value of a second type of the operational data, the values of two types (e.g., parameters) being equal or within a threshold difference, or the values of two or more parameters satisfying some other functional relationship. Determining a value indicative of the thermoregulatory activity of the patient based on relationships among two or more parameters is described further in relation to FIG. 5.

The temperature management system can determine that operational data satisfy a particular trend. For example, the temperature management system can determine that a value of the operational data is increasing, decreasing, oscillating, or performing some other trend. For example, the temperature management system can determine that a response time of the patient's temperature to be the control temperature is too fast or too slow with respect to a threshold response time. The temperature management system can determine that a derivative of the value of the operational data satisfies a threshold. The temperature management system can determine that the value of the operational data is a threshold difference from a historical average.

The processor determines, from the values of the operational data, a value indicative of a thermoregulatory activity of the patient by comparing the values to the rules. If a rule (or set of rules) is satisfied, the processor can generate an alert for notifying a user of the value indicative of a thermoregulatory activity of the patient. The alert can be generated for presentation on a user interface of the temperature management system. The processor can send the alert to one or more other computing devices, such as computing devices associated with a health care provider of the patient. In an aspect, a display device is configured to communicate with the processor, wherein the data representing the alert indicating the value indicative of a thermoregulatory activity of the patient causes a notification to be displayed on the display device.

The value indicative of a thermoregulatory activity of the alert generated by the processor can indicate a general health condition of the patient. Generally, the alert is raising a red flag that there may be prognostic or predictive information based on degree of injury or compromise to thermoregulatory capability. The alert provides an indicator for a health care provider to investigate the patient's condition further regarding a clinical state or underling condition of the patient. In some implementations, the processor generates the alert to cause one or more devices to perform an action. For example, feedback can be presented to a healthcare provider, such as an audio cue, visual presentation, and so forth. The alert can cause a device to contact a healthcare provider (e.g., place a phone call or page to a physician, nurse, etc.). The alert can cause a device to display particular data about the patient, such as a presentation of the patient's temperature over a given time window. The alert can cause a device to update a health record associated with the patient or cause the device to retrieve a health record associated with the patient for further analysis. In certain implementations, the processor of the system may be configured to determine if the alert is a real time alert or recorded for retrospective review. If it is a real time, it may then determine whether it's displayed to the screen, transmitted further in an information chain, or displayed to a third-party monitor. An example route is to send the alert to a physician or nurse's cell phone. The alert may open a cell phone-based application or open an Internet-based application. From either application the physician or nurse could see the alert plus other relevant data that may have been transmitted. The alert may include a hospital specific patient identifier, but otherwise be invisible as to the identity of the patient, unless the physician or the hospital has added the patient name to either the application on their phone or to the Internet. The alert may include a non-patient specific identifier such as a bed number. Additionally, the physician would have the opportunity to take actions in response to receiving the alert. This might include triggering a phone call to the ICU desk, adjusting the temperature change range or duration of the change on the alert (in the application or remote to the temperature management system) or marking that the physician has seen the alert. Changing the duration or range would allow the user to set a duration so that a transient spike would not trigger the alert. E.g., a deviation of 0.4 C sustained for five minutes might trigger an alert, while a pause in therapy would disable this alert—but could trigger a different alert. In the case of adjusting the time and/or duration of the alert, such an adjustment may only affect the notification to that specific person. For example, adjusting the temperature change alert range from a 0.4 C temperature change to a 0.5 C temperature change, but leaving the duration the same may affect whether the application sounds a tone/alert on that physician's specific application or web-based program. The data would still be collected in the system for retrospective or other review. This way a dual alert to a nurse or physician might have different alert ranges and actions. The described features may put the user, e.g., physician in complete control. For example, the first point of control may be at the bedside, where the alert ranges may be set. The second point of control may be at the receiving application or website where the user may adjust nominal settings, e.g., for "tones". As such, two or more triggers may be established: the first is to "send" the alert from the machine into the network to the receiving device; and the second is the action that the receiving device takes upon receiving the alert. A scheduling feature may also be provided that allows for the transfer data from one physician going off shift to another coming on shift. A response tree may be provided that requires an acknowledgement that the alert has been seen or transferred from one physician to another. For example, a first doctor is given 5 minutes to acknowledge receipt of the alert, and if no acknowledgment is made, the alert is sent to another physician or nurse. In certain implementations, one or more of the various alerts or alert parameters described herein may be customized by the user. Multiple options for alert delivery, e.g., device display, nurse's station, EMR, cell phone, etc. may be set.

The processor can determine a value indicative of a thermoregulatory activity of the patient and generate the alert by analyzing the values of the operational data responsive to the controlling of the patient's body temperature by the heat exchange system 10. In some implementations, the processor determines the value indicative of a thermoregulatory activity of the patient during the controlling. In some implementations, the processor can communicate with a data storage storing values of the operational data for a given time period. The processor can determine the value indicative of a thermoregulatory activity of the patient for a given instant in time during the given time period or the value indicative of a thermoregulatory activity of the patient over the course of the given time period.

In some implementations, the alert can indicate that the values of the operational data are indicative of a particular thermoregulatory activity of the patient. For example, the processor can determine whether the patient is fighting the temperature management of the heat exchange system 10 and how much the patient is fighting the temperature management. The processor is configured to generate a rating indicating this relative thermoregulatory capability of the patient.

Figure 7A:
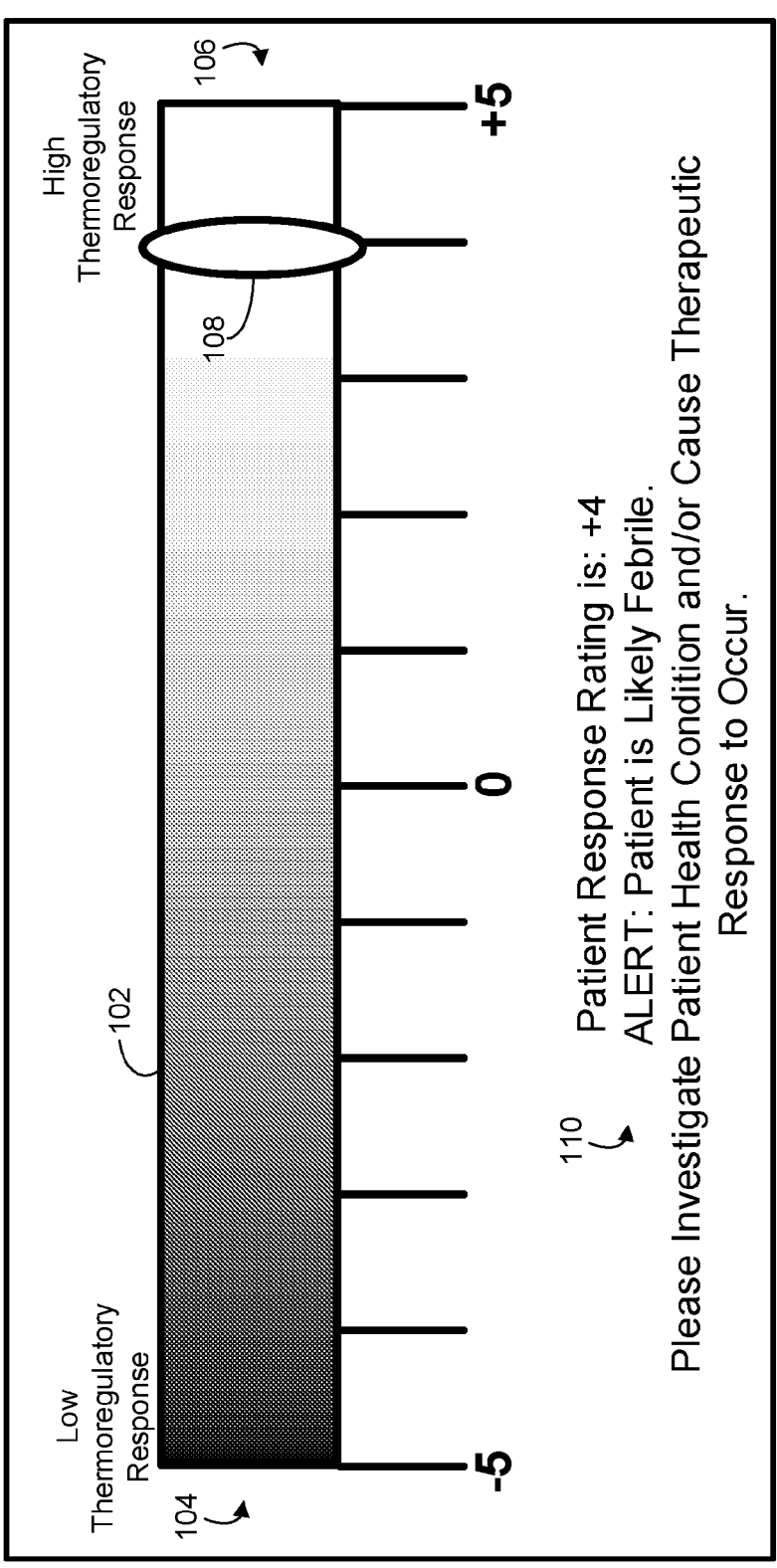
FIGS. 7A-7B show example user interfaces presenting alerts.
Figure 7B:
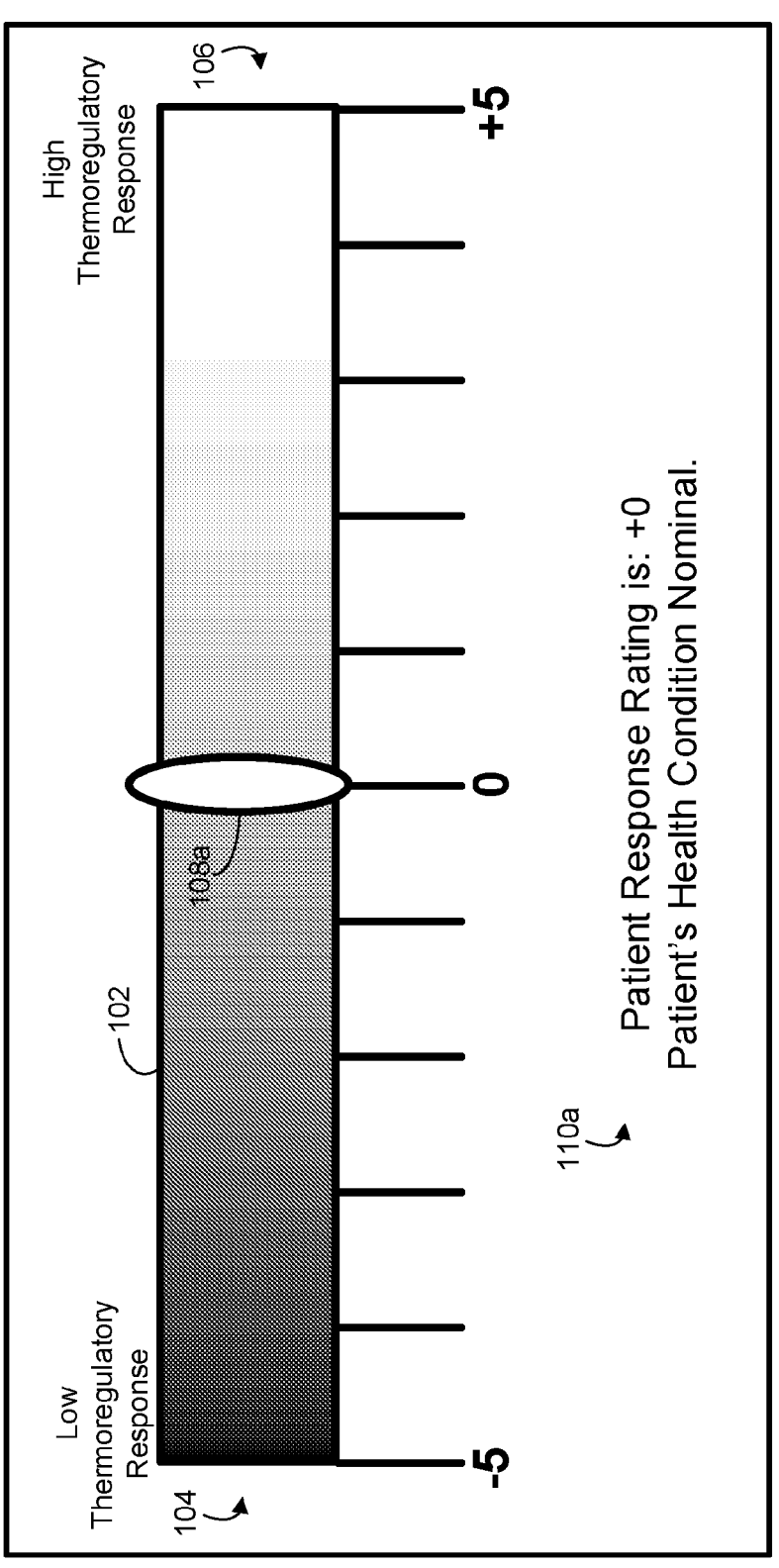

FIG. 7A shows an example user interface 100 including a visual presentation of an alert. The user interface includes a number scale 102 rating how responsive a patient's thermoregulatory system is to controlling temperature by the heat exchange system 10. The scale 102 includes a low thermoregulatory response portion 104 indicating that the patient is not resisting temperature control or is exhibiting a weak thermoregulatory response to temperature control. The scale 102 includes a high thermoregulatory response portion 106 indicating that the patient is resisting temperature control completely or is exhibiting a strong thermoregulatory resistance to temperature control. In other words, portion 104 is indicative of thermoregulatory compliance, and portion 106 is indicative of the patient being febrile. The alert can show the rating as a marker 108. In some implementations, the number scale can be relative to a target temperature (e.g., represented at 0 or some other value on the number scale). The number scale can include a gradient or other means of indicating the value indicative of a thermoregulatory activity of the patient. A clinical indication can dictate where the patient's response level should be on the scale. The user interface 100 can include test 110 stating the value of the patient's response on the scale 102. In some implementations, the text 110 (or audio cue, etc.) can indicate a likely status of the thermoregulatory activity of the patient and a recommendation to investigate the thermoregulatory activity of the patient further. Turning to FIG. 7B, in some implementations, a message 110a and/or indicator 108a can indicate that a patient's status is nominal such that the thermoregulatory response of the patient does not show an adverse health condition.

In some implementations, the alert includes a score. The score can be indicative of a patient presenting an underlying hyperthermic state or hypothermic state, rather than a response level. For example, the score can be a function of an estimated "base" body temperature of the patient if the heat exchange system 10 were not controlling the body temperature of the patient. The score can be the estimated base body temperature. In some implementations, the score indicates that the patient has a damaged or compromised endogenous thermoregulatory mechanism. For example, a lower score can indicate that the patient is less capable of self-regulating body temperature than a capability represented by higher score, and if a score below a threshold value is detected, the alert can include a warning to investigate the endogenous thermoregulatory mechanism of the patient.

In some implementations, responsive to data indicative of a low response level, the processor is configured to test the response level by changing the control temperature of the patient's body and measuring the response in a test. The test may raise or lower the target temperature and closely monitor (e.g., taking additional data as needed) the patient's response to determine if the response mechanism is damaged. For example, a response time can be measured that indicates how long it takes to change the patient's body temperature to the new control value. The response time can be compared to an expected response time for such a change. The results of the test can be presented to a health care provider. Thus, the temperature management system can determine an effectiveness of the endogenous thermoregulatory mechanism of the patient in changing the patient's body temperature. For example, the processor can measure a value representing a cooling power required to change the patient's body temperature n degrees over a predefined time interval, which is indicative of an effectiveness of the endogenous thermoregulatory mechanism of the patient in changing the patient's body temperature.

In an aspect, the temperature management system is configured to cause one or more actions for a therapeutic response to a determination that the patient has an anomalous thermoregulatory health condition. The therapeutic response can include a treatment by the heat exchange system 10, such as heating or cooling the patient. The therapeutic response can be caused in another device by the processor, such as an injection of a drug. In some implementations, the therapeutic response is performed by a health care provider, such as giving the patient medication or applying another form of treatment. For example, the temperature management system can cause the heat exchange device or another device of the heat exchange system 10 to change operation in order to accommodate the anomalous thermoregulatory activity. If the patient has a weak thermoregulatory response, the temperature management system can cause the heat exchange system 10 to reduce a cooling or heating effort for controlling the patient's body temperature. If the patient has a strong thermoregulatory response, the temperature management system can cause the heat exchange system 10 can increase a cooling or heating effort for controlling the patient's body temperature. The temperature management system can send a command to another system (e.g., another medical device) that is assisting with treatment of the patient to help that device take corrective action. As stated previously, the temperature management system can cause a message to be sent to another device to alert a health care provider to take corrective action.

In an aspect, the processor of the temperature management system is configured to cause the temperature management system to transmit (e.g., over a wireless or wired network) the data representing the alert indicating the value indicative of the thermoregulatory activity of the patient to a remote device associated with a treatment provider. For example, the transmitting the data representing the alert including the value indicative of the thermoregulatory activity of the patient to the remote device can include triggering a phone call, text message or email. The remote device may comprise the user interface.

In an aspect the temperature sensor 56 of the heat exchange system 10 measures a blood temperature of the patient, as described previously with respect to FIG. 1. The temperature management system is configured to determine the value indicative of the thermoregulatory activity of the patient responsive to changes in the blood temperature of the patient. For example, the temperature management system can determine a value indicative of the thermoregulatory activity of the patient responsive not only to detecting particular values of the operational data of the heat exchange system 10 but also in response to detecting corresponding values of the blood temperature. The temperature management system can measure a rate of change value of the blood temperature in the patient. This process is similar to the process of measuring the rate of change of the body temperature of the patient as described above for determining the thermoregulatory response of the patient. If the rate of change of the blood temperature of the patient exceeds a threshold rate of change, the temperature management system can determine that the patient has a weak thermoregulatory response. Likewise, if the rate of change is below a threshold value, the temperature management system can determine that the patient has a strong thermoregulatory response (and may be febrile or have an infection).

Turning to FIG. 4, an example process 400 is shown for determining a value indicative of the thermoregulatory activity of a patient using data describing the operation of the heat exchange system 10 of FIGS. 1-3. The processor of the temperature management system 10 receives (402) the temperature data from the sensor indicative of the temperature of the body of the patient. The processor controls (404), based on the temperature data, the heat exchange device to maintain the temperature of the body of the patient within a target temperature range. The processor receives (406), in response to the controlling, the operational data representing operation of the heat exchange system. The processor determines (408), based on the temperature data and the operational data, a value indicative of a thermoregulatory activity of the patient. The processor generates (410) an alert though the user interface. The alert can indicate a status of the thermoregulatory condition of the patient, including the value. The processor determines (412) whether the value indicative of the thermoregulatory activity requires a therapeutic response. If a response is needed, the processor is configured to cause (414) the therapeutic response by the heat exchange system (if applicable) or another device for treating the health condition of the patient. The therapeutic response can include raising or lowering the patient's temperature, causing another device to measure a physiological parameter (e.g., data value) of the patient to gather more data about the potentially adverse health condition of the patient, and so forth. If no response is needed, the processor is configured to generate (414), based on the value, an alert via the user interface of the temperature management system.

Turning to FIG. 5, a process 500 is shown for determining a value indicative of a thermoregulatory activity of a patient using data describing the operation of the heat exchange system 10 of FIGS. 1-3. Using the process 500, the processor of the temperature management system is configured to determine the value indicative of a thermoregulatory activity of the patient by analyzing two or more types of operational data and their relationship to one another. In some implementations, as previously described, values of two or more types of operational data can form a profile that is associated with a particular thermoregulatory activity, either based on training machine learning models or by some other calibration mechanism. The processor of the temperature management system receives temperature data from a sensor indicative of the temperature of the body of the patient. The processor controls, based on the temperature data, the heat exchange system to maintain the temperature of the body of the patient within a target temperature range. The processor (e.g., a processor) is configured to receive (502) a first type of operational data and receive (504) a second type of operational data.

The processor is configured to determine (506) that a relationship between the value of the first type of the operational data and the value of the second type of the operational data is satisfied. The relationship can include a comparison of trends of the values of the two or more types of the operational data. For example, the relationship can be satisfied if the value for the first type of data is increasing over time while the value for the second type of data is decreasing over time, or the second value is also increasing over time, and so forth. The relationship can include a mathematical function. For example, the relationship can be satisfied if the values of the two or more types of operational data add to a particular value of a third type of operational data or within a threshold difference of the third type of the operational data. The relationship can be between rates of change of the two values. For example, the relationship can be satisfied if the first value is decreasing or increasing more quickly than the second value. Other such relationships can be determined between two types of operational data or among a plurality of types of operational data.

In some implementations, the processor determines that the relationship between the value of the first type of operational data and the value of the second type of operational data is satisfied by determining that the value of the first type of operational data exceeds a first threshold and determining that the value of the second type of operational data exceeds a second threshold. In some implementations, the processor determines that the relationship between the value of the first type of operational data and the value of the second type of operational data is satisfied by determining that the value of the first type of operational data is within a first predetermined value range and determining that the value of the second type of operational data is within a second predetermined value range. Other such comparisons are possible.

In some implementations, the processor compares the profile of values of the operational data to a plurality of relationships to determine whether multiple relationships are satisfied. In some implementations, different combinations of satisfied relationships among the values or types of operational data can each indicate a thermoregulatory activity. The relationships can each be tested to operate as a voting system for which type of thermoregulatory activity the patient may be experiencing, and the processor can output a probability associated with the alert indicating a likelihood that the patient has a thermoregulatory activity such as being febrile or having an infection.

The processor determines (508), responsive to determining whether one or more relationships are satisfied, a value indicative of a thermoregulatory activity of the patient corresponding to the relationship that is satisfied. The processor generates (510), based on the value, an alert via the interface representing the thermoregulatory activity of the patient. The processor can determine (512) whether the thermoregulatory activity of the patient requires a therapeutic response and cause (514) the response, similar to the process 400 described in relation to FIG. 4. In some implementations, the therapeutic response by the heat exchange system or another system or device includes an automatic injection or infusion of a supplemental fluid. For example, the automatic injection or infusion is an injection or infusion of an anti-shivering medication. In some implementations, the therapeutic response by the heat exchange system comprises raising or lowering a body temperature of the patient.

In some implementations, the types of the operational data comprise two or more of a flow rate of heat exchange fluid circulating through the heat exchange device, a pressure of heat exchange fluid circulating through the heat exchange device, a temperature of heat exchange fluid circulating through the heat exchange device, a temperature of heat exchange plates in the heat exchange device, and a pump speed of a pump of the heat exchange device. The temperature management system can be configured to use values of operational data and compare them for a heat exchange device including a catheter and/or surface pad for exchanging heat with the patient.

Turning to FIG. 6, a process 600 is shown for determining a value indicative of a thermoregulatory activity of a patient using data describing the operation of the heat exchange system 10 of FIGS. 1-3. The processor of the temperature management system receives (602) the temperature data from the sensor indicative of the temperature of the body of the patient. The processor controls (604), based on the temperature data, the heat exchange system 10 to maintain the temperature of the body of the patient within a target temperature range. The processor of the temperature management system is configured to receive (606) one or more types of operational data. As previously described, the types of operational data can include e.g., one or more of a flow rate of heat exchange fluid circulating through the heat exchange device, a pressure of heat exchange fluid circulating through the heat exchange device, a temperature of heat exchange fluid circulating through the heat exchange device, a temperature of heat exchange plates in the heat exchange device, and a pump speed of a pump of the heat exchange device, or another type of operational data. In some implementations, the heat exchange device of the heat exchange system 10 includes a catheter or surface pad for exchanging heat with the patient, and the types of the operational data are specific to the pad and/or the catheter.

The processor determines (608) a value indicative of a thermoregulatory activity of the patient corresponding to the value of the operational data. The processor causes (610), in response to determining the value, a therapeutic response by the heat exchange system or an additional device for treating the thermoregulatory activity of the patient. In some implementations, the therapeutic response by the heat exchange system 10 or other device includes an automatic injection or infusion of a supplemental fluid. In some implementations, the automatic injection or infusion is an injection or infusion of an anti-shivering medication. In some implementations, the therapeutic response by the heat exchange system includes raising or lowering a body temperature of the patient.

FIG. 8 shows a flow diagram including an example process 800 for determining a value indicative of a thermoregulatory activity of a patient using data regarding a flow rate of the heat exchange system of FIGS. 1-3. A processor of the temperature management system is configured to control (802) the heat exchange device, based on temperature data received from a temperature sensor of a heat exchange system, to maintain a body temperature of a patient within a target temperature range. The processor of the temperature management system is configured to receive (804), in response to the controlling, operational data representing a flow rate of heat exchange fluid (e.g., a working fluid, a refrigerant, etc.) of the heat exchange system. The working fluid can include a saline solution or other fluid for cooling or heating the body of the patient. The working fluid can be configured to heat or cool a heat exchange device, such as a catheter or cooling/heating pads. Measuring the flow rate of the working fluid can indicate how much fluid is being used to cool the patient. A higher flow rate may mean more fluid over time is required to cool the patient, and therefore the patient could have a more active thermoregulatory response, which is resisting cooling by the heat exchange device. A lower flow rate may mean less fluid over time is required to cool the patient, and therefore the patient could have a relatively less active thermoregulatory response, which is providing less resistance to cooling by the heat exchange device. To increase the degree of certainty that the measured flow rate is in fact a result of the patient's hyperactive or impaired thermoregulatory activity, the processor may also factor in the patient's measured temperature or rate of change of temperature. In another embodiment, to increase the degree of certainty that the measured flow rate is in fact a result of the patient's hyperactive or impaired thermoregulatory activity, the processor may factor in the difference or change in the temperature ($\Delta T$) of the heat exchange fluid, e.g., saline, going into the heat exchange device such as a catheter, and the heat exchange fluid coming out of the heat exchange device, or the processor may factor in the temperature of the heat exchange plates.

To measure the flow rate of the heat exchange fluid, the system is configured to measure the flow rate over a time period of operation of the heat exchange system 10, e.g., over a 24 hour period. The processor may calculate an average for recorded flow rates, e.g., the average for recorded flow rates over the last 24 hours for the patient being treated. The processor of the temperature management system compares (806) the measured flow rate or average measured flow rate to a threshold value, such as a normal operational range for working fluid flow rate for a heat exchange system 10. For example, a normal operational working fluid flow rate range is 50 ml/min to 300 ml/min while maintaining a patient at a constant temperature. The processor may retrieve the normal operational range for working fluid flow rate by accessing a look up table stored locally on the system memory or in a remote database. The processor of the temperature management system is configured to determine (808), based on the comparison, a value indicative of the thermoregulatory activity of the patient. For example, if the measured flow rate is higher than the threshold value for a sustained period of time (e.g., 10-20 ml/min above 300 ml/min for 10-30 minutes), the processor of the temperature management system can determine a value for the thermoregulatory activity, which is higher than normal. This higher than normal thermoregulatory activity value is alerted to the caregiver, and may indicate that the patient is suffering from an infection and is febrile. If the measured flow rate is lower than the threshold value for a sustained period of time (e.g., 10-20 ml/min below 50 ml/min for 5-10 minutes) the processor of the temperature management system can determine a value for the thermoregulatory activity that is lower than normal. This lower than normal thermoregulatory activity value is alerted to the caregiver, and may indicate that the patient is suffering from neurological damage or another condition affecting the patient's thermoregulatory response. The processor of the temperature management system generates (810) an alert by a user interface responsive to the determining. The alert can be in the form of a number scale where a value below 0 down to −5 equals lower than normal thermoregulatory activity and a value above 0 up to +5 equals higher than normal thermoregulatory activity, with 0 representing normal thermoregulatory activity.

In response to the determining step, the processor of the temperature management system can determine (812) whether the patient should receive a therapeutic response. If a therapeutic response is needed, the temperature management system causes (814) either the heat exchange system or another device or system to apply the response for treating the patient. For example, the heat exchange system 10 may cause a reduction in the temperature of the refrigerant or saline fluid circulating through the heat exchange device to increase cooling of the patient. Optionally, the system may prompt the caregiver to approve the therapeutic response prior to the response occurring.

FIG. 9 shows a flow diagram including an example process 900 for determining a value indicative of a thermoregulatory activity of a patient using data regarding a fluid pressure of the heat exchange system of FIGS. 1-3. A processor of the temperature management system is configured to control (902) the heat exchange system 10 based on temperature data received from a temperature sensor of a heat exchange system to maintain a body temperature of a patient within a target temperature range. The processor of the temperature management system is configured to receive (904), in response to the controlling, operational data representing a pressure of heat exchange fluid (e.g., a working fluid, a refrigerant, etc.) of the heat exchange system. The working fluid can include a saline solution or other fluid for cooling or heating the body of the patient. The working fluid can be configured to heat or cool a portion of the heat exchange system, such as a catheter, or cooling/heating pads. Measuring the pressure of the heat exchange fluid can indicate how much fluid is being used to cool the patient. A higher fluid pressure could mean more fluid is required to cool the patient, and therefore the patient could have a more active thermoregulatory response, which is resisting cooling by the heat exchange device. A lower fluid pressure could mean less fluid is required to cool the patient, and therefore the patient could have a relatively less active thermoregulatory response, which is providing less resistance to cooling by the heat exchange device. To increase the degree of certainty that the measured fluid pressure is in fact a result of the patient's hyperactive or impaired thermoregulatory activity, the processor may also factor in the patient's measured temperature or rate of change of temperature. In another embodiment, to increase the degree of certainty that the measured fluid pressure is in fact a result of the patient's hyperactive or impaired thermoregulatory activity, the processor may factor in the difference or change in the temperature ($\Delta T$) of the heat exchange fluid, e.g., saline, going into the heat exchange device such as a catheter, and the heat exchange fluid coming out of the heat exchange device, or the processor may factor in the temperature of the heat exchange plates.

To measure the fluid pressure in the heat exchange system 10, the system is configured to measure the pressure from a pressure sensor located in the heat exchange system, e.g., in a working fluid conduit, or in a cassette heat exchanger through which working fluid flows. The processor of the heat exchange system 10 compares (906) the measured pressure to a threshold value, such as a normal operational range for working fluid pressures for a heat exchange system 10. For example, a normal operational range for working fluid pressure is 20 to 40 psi while maintaining a patient at a constant temperature. The processor may retrieve the standard operational range of values for fluid pressures by accessing a look up table stored locally on the system memory or in a remote database. The processor of the temperature management system is configured to determine (908), based on the comparison, a value indicative of a thermoregulatory activity of the patient. For example, if the measured fluid pressure is higher than the threshold value for a sustained period of time (e.g., 5-10 psi above 40 psi for 10-30 min), the processor of the temperature management system can determine a value for the thermoregulatory activity, which is higher than normal. This higher than normal thermoregulatory activity value is alerted to the caregiver, and may indicate that the patient is suffering from an infection and is febrile. If the measured fluid pressure is lower than the threshold value, (e.g., 5-10 psi below 20 psi for 10-30 min) the processor of the temperature management system can determine a value for the thermoregulatory activity that is lower than normal. This lower than normal thermoregulatory activity value is alerted to the caregiver, and may indicate that the patient is suffering from neurological damage or other condition affecting the patient's thermoregulatory response. The processor of the temperature management system generates (810) an alert by a user interface responsive to the determining. The alert can be in the form of a number scale where a value below 0 down to −5 equals lower than normal thermoregulatory activity and a value above 0 up to +5 equals higher than normal thermoregulatory activity, with 0 representing normal thermoregulatory activity.

In response to the determining step, the processor of the temperature management system can determine (912) whether the patient should receive a therapeutic response. If a therapeutic response is needed, the temperature management system causes (914) either the heat exchange system

10 or another device or system to apply the response for treating the patient. For example, the temperature management system may cause an infusion pump, coupled to the heat exchange system 10, to infuse an anti-shivering medication upon approval by a caregiver. Optionally, the system may prompt the caregiver to approve the infusion of medication prior to the response occurring.

FIG. 10 shows a flow diagram including an example process 1000 for determining a value of a thermoregulatory activity of a patient using data regarding the change in temperature of the heat exchange fluid of the heat exchange system of FIGS. 1-3. A processor of the temperature management system is configured to control (1002) a heat exchange system, based on temperature data received from a temperature sensor of a heat exchange system, to maintain a body temperature of a patient within a target temperature range. The processor of the temperature management system is configured to receive (1004), in response to the controlling, operational data representing a temperature of heat exchange fluid of the heat exchange system. The heat exchange fluid can include a refrigerant, saline solution or other fluid for cooling or heating the body of the patient. The heat exchange fluid can be configured to heat or cool a portion of the heat exchange system, such as thermal plates, a heat exchange cassette, a catheter or cooling/heating pads. Measuring the difference or change in the temperature ($\Delta T$) of the heat exchange fluid, e.g., saline, going into the heat exchange device such as a catheter, and the heat exchange fluid coming out of the heat exchange device, e.g., catheter, may provide information regarding the patient's thermoregulatory activity. For example, a large temperature change (delta-T) may mean the heat exchange system is expending more effort to cool the patient, and therefore the patient could have a more active thermoregulatory response, which is resisting cooling by the heat exchange device. A smaller temperature change may mean the heat exchange system 10 is expending less effort to cool the patient, and therefore the patient could have a relatively less active thermoregulatory response, which is providing less resistance to cooling by the heat exchange device. To increase the degree of certainty that the measured change in temperature of the heat exchange fluid is in fact a result of the patient's hyperactive or impaired thermoregulatory activity, the processor may also factor in the patient's measured temperature or rate of change of temperature.

In some implementations, to measure the change in temperature of the heat exchange fluid, the heat exchange system 10 is configured to measure the temperature of the heat exchange fluid from a first temperature sensor located in the fluid supply pathway going into the catheter and a second temperature sensor located in the fluid return pathway coming out of the catheter. The processor of the temperature management system compares (1006) the measured delta T value of the heat exchange fluid to a threshold delta-T value, such as a normal range of delta-T values observed in the treatment of patients exhibiting normal thermoregulatory activity. For example, a normal range of delta-T values for heat exchange fluid is 5 degrees Celsius (C.) to 12 degrees C. while maintaining a patient at a constant temperature. The processor may retrieve the normal range of delta-T values by accessing a look up table stored locally on the system memory or in a remote database. The processor of the temperature management system is configured to determine (1008), based on the comparison, a value indicative of a thermoregulatory activity of the patient. For example, if the measured delta T is higher than the threshold value, (e.g., 2-5 degrees C. above a delta T of 12 degrees C.

for 10-30 min) the processor of the temperature management system can determine a value for the thermoregulatory activity, which is higher than normal. This higher than normal thermoregulatory activity value is alerted to the caregiver, and may indicate that the patient is suffering from an infection and is febrile. If the measured delta-T is lower than the threshold value, (e.g., 2-5 degrees C. below a delta T of 5 degrees C. for 10-30 min) the processor of the temperature management system can determine a value for the thermoregulatory activity that is lower than normal. This lower than normal thermoregulatory activity value is alerted to the caregiver, and may indicate that the patient is suffering from neurological damage or other condition affecting the patient's thermoregulatory response. The processor of the temperature management system generates (810) an alert by a user interface responsive to the determining. The alert can be in the form of a number scale where a value below 0 down to −5 equals lower than normal thermoregulatory activity and a value above 0 up to +5 equals higher than normal thermoregulatory activity, with 0 representing normal thermoregulatory activity.

In response to the determining step, the processor of the temperature management system can determine (812) whether the patient should receive a therapeutic response. If a therapeutic response is needed, the temperature management system causes (814) either the heat exchange system 10 or another device or system to apply the response for treating the patient. For example, the heat exchange system 10 may cause a reduction in the temperature of the working fluid circulating through the heat exchange device to increase cooling of the patient. Optionally, the system may prompt the caregiver to approve the therapeutic response prior to the response occurring, FIG. 11 shows a flow diagram including an example process 1100 for determining a value of a thermoregulatory activity of a patient using data regarding the temperature of the heat exchange plates of the heat exchange system of FIGS. 1-3. A processor of the temperature management system is configured to control (1102) a heat exchange device, based on temperature data received from a temperature sensor of a heat exchange device, to maintain a body temperature of a patient within a target temperature range. The processor of the temperature management system is configured to receive (1104), in response to the controlling, operational data representing a temperature of heat exchange plates (e.g., such as the heat exchange plates described herein for heating or cooling a working fluid circulating through a heat exchange cassette positioned between the heat exchange plates). Measuring the temperature of the heat exchange plates may provide information regarding a patient's thermoregulatory activity. For example, a high plate temperature may mean the heat exchange system 10 is expending more effort to cool the patient, and therefore the patient could have a more active thermoregulatory response, which is resisting cooling by the heat exchange device. A lower plate temperature may mean the heat exchange system is expending less effort to cool the patient, and therefore the patient could have a relatively less active thermoregulatory response, which is providing less resistance to cooling by the heat exchange device. To increase the degree of certainty that the measured temperature of the heat exchange plates is in fact a result of the patient's hyperactive or impaired thermoregulatory activity, the processor may also factor in the patient's measured temperature or rate of change of temperature.

In some implementations, to measure the temperature of the heat exchange plates, the heat exchange system 10 includes a temperature sensor on or in one or more of the plates. The processor of the temperature management system can compare (1106) the measured absolute plate temperature to a threshold value, such as a normal operational range of temperatures for the heat exchange plates of a heat exchange system 10 observed in the treatment of patients exhibiting normal thermoregulatory activity. For example, a normal operational range for plate temperatures is 5-30 degrees C. while maintaining a patient at a constant temperature. The processor may retrieve the normal operational range of values for plate temperature by accessing a look up table stored locally on the system memory or in a remote database. The processor of the temperature management system is configured to determine (1108), based on the comparison, a value indicative of a thermoregulatory activity of the patient. For example, if the measured temperature is higher than the threshold value, (e.g., 5 degrees C. above 30 degrees C. for 10-30 min) the processor of the temperature management system can determine a value for the thermoregulatory activity, which is higher than normal. This higher than normal thermoregulatory activity value is alerted to the caregiver, and may indicate that the patient is suffering from an infection and is febrile. If the measured temperature is lower than the threshold value, (e.g., below 5 degrees Celsius for 10-30 min) the processor of the temperature management system can determine a value for the thermoregulatory activity that is lower than normal. This lower than normal thermoregulatory activity value is alerted to the caregiver, and may indicate that the patient is suffering from neurological damage or other condition affecting the patient's thermoregulatory response. The alert can be in the form of a number scale where a value below 0 down to −5 equals lower than normal thermoregulatory activity and a value above 0 up to +5 equals higher than normal thermoregulatory activity, with 0 representing normal thermoregulatory activity.

In response to the determining step, the processor of the temperature management system can determine (812) whether the patient should receive a therapeutic response. If a therapeutic response is needed, the temperature management system causes (814) either the heat exchange system or another device or system to apply the response for treating the patient. For example, the heat exchange system 10 may cause a reduction in the temperature of the refrigerant circulating through the heat exchange plates to increase cooling of the patient. Optionally, the temperature management system may prompt the caregiver to approve the therapeutic response prior to the response occurring.

FIG. 12 shows a flow diagram including an example process 1200 for determining a value of a thermoregulatory activity of a patient using data regarding the pump speed of the heat exchange fluid pump in the heat exchange system of FIGS. 1-3. A processor of the temperature management system is configured to control (1202) a heat exchange system, based on temperature data received from a temperature sensor of the heat exchange system, to maintain a body temperature of a patient with in a target temperature range. The processor of the temperature management system is configured to receive (1204), in response to the controlling, operational data representing a pump speed of a heat exchange fluid pump of the heat exchange system 10 (e.g., for pumping/circulating a working fluid, such as saline through a catheter). Measuring the pump speed can indicate how much fluid is being used to cool the patient. A faster pump speed may mean more fluid over time is required to cool the patient, and therefore the patient could have a more active thermoregulatory response, which is resisting cooling by the heat exchange device. A slower pump speed may mean less fluid over time is required to cool the patient, and therefore the patient could have a relatively less active thermoregulatory response, which is providing less resistance to cooling by the heat exchange device. To increase the degree of certainty that the measured pump speed is in fact a result of the patient's hyperactive or impaired thermoregulatory activity, the processor may also factor in the patient's measured temperature or rate of change of temperature. In another embodiment, to increase the degree of certainty that the measured pump speed is in fact a result of the patient's hyperactive or impaired thermoregulatory activity, the processor may factor in the difference or change in the temperature ($\Delta T$) of the heat exchange fluid, e.g., saline, going into the heat exchange device such as a catheter, and the heat exchange fluid coming out of the heat exchange device, or the processor may factor in the temperature of the heat exchange plates.

In some implementations, to measure the pump speed, the heat exchange system 10 includes a tachometer, encoder, or other sensor in communication with the pump (e.g., to measure rotor speed). The processor of the temperature management system can compare (1206) the measured pump speed to a normal pump speed observed in the treatment of patients exhibiting normal thermoregulatory activity while maintaining a patient at a constant temperature, e.g., 5-20 rpm. The processor may retrieve the normal pump speed range by accessing a look up table stored locally on the system memory or in a remote database. The temperature management system is configured to determine (1208), based on the comparison, a value indicative of a thermoregulatory activity of the patient.

For example, if the pump speed is higher than the normal range (e.g., 5 rpm higher than the top of the normal range for 10-30 min), the processor of the temperature management system can determine a value for the thermoregulatory activity, which is higher than normal. This higher than normal thermoregulatory activity value is alerted to the caregiver, and may indicate that the patient is suffering from an infection and is febrile. If the pump speed is lower than the normal range, (e.g., 5 rpm lower than the bottom of the normal range for 10-30 min) the processor of the temperature management system can determine a value for the thermoregulatory activity that is lower than normal. This lower than normal thermoregulatory activity value is alerted to the caregiver, and may indicate that the patient is suffering from neurological damage or other condition affecting the patient's thermoregulatory response. The processor of the temperature management system generates (810) an alert by a user interface responsive to the determining. The alert can be in the form of a number scale where a value below 0 down to −5 equals lower than normal thermoregulatory activity and a value above 0 up to +5 equals higher than normal thermoregulatory activity, with 0 representing normal thermoregulatory activity.

In certain embodiments, the processor may be configured to receive measured values of two or more types of any of the above types of operational data simultaneously to increase the degree of certainty that the measured operational data values are in fact a result of the patient's hyperactive or impaired thermoregulatory activity, rather than a system artifact or system problem. The processor may also factor in the patient's measured temperature, or rate of change of temperature, in determining a value indicative of thermoregulatory activity in any of the examples described herein. For example, the fact that the measured patient temperature decreases less than expected or at a slower rate than expected compared to historical data of patients treated with identical temperature management systems may increase the degree of certainty that the measured values of operational data are due to the patient's hyperactive thermoregulatory activity. To further increase the degree of certainty that the measured values of operational data are in fact a result of the patient's hyperactive or impaired thermoregulatory activity, the processor may also factor in the catheter heat exchange fluid outlet temperature. To further increase the degree of certainty that the measured values of operational data are in fact a result of the patient's hyperactive or impaired thermoregulatory activity, the processor may also factor in an estimate of the patient's weight (e.g., the estimate of the patient's weight may be preprogramed based on historical norms or input by a user). In another embodiment, the value indicative of a thermoregulatory activity may be determined using machine learning, which factors in two or more types of the operational data and patient data, such as patient temperature data. The value indicative of a thermoregulatory activity may be determined using a mathematical model, which factors in two or more types of the operational data described herein, e.g., the mathematical model may be a statistical model built via machine learning. For example, to use machine learning which factors in the two or more types of operational data, the temperature management system can be configured to receive, at machine learning logic, two or more types of the operational data and apply the machine learning logic to the two or more types of the operational data.

The alert for thermoregulatory activity may include other forms. For example, a color scale or audible alert may be output via the user interface to provide a value indicative of thermoregulatory activity.

Some implementations of subject matter and operations described in this specification (e.g., processes 400, 500, 600, 800, 900, 1000, 1100, and 1200) can be implemented in digital electronic circuitry, or in computer software, firmware, or hardware, including the structures disclosed in this specification and their structural equivalents, or in combinations of one or more of them. For example, in some implementations, the processor of the temperature management system can be implemented using digital electronic circuitry, or in computer software, firmware, or hardware, or in combinations of one or more of them.

Some implementations described in this specification (e.g., the processor of the temperature management system, etc.) can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. In some implementations, the query response module 104 and/or the data structure module 106 comprises a data processing apparatus as described herein. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed for execution on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD-ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 13:
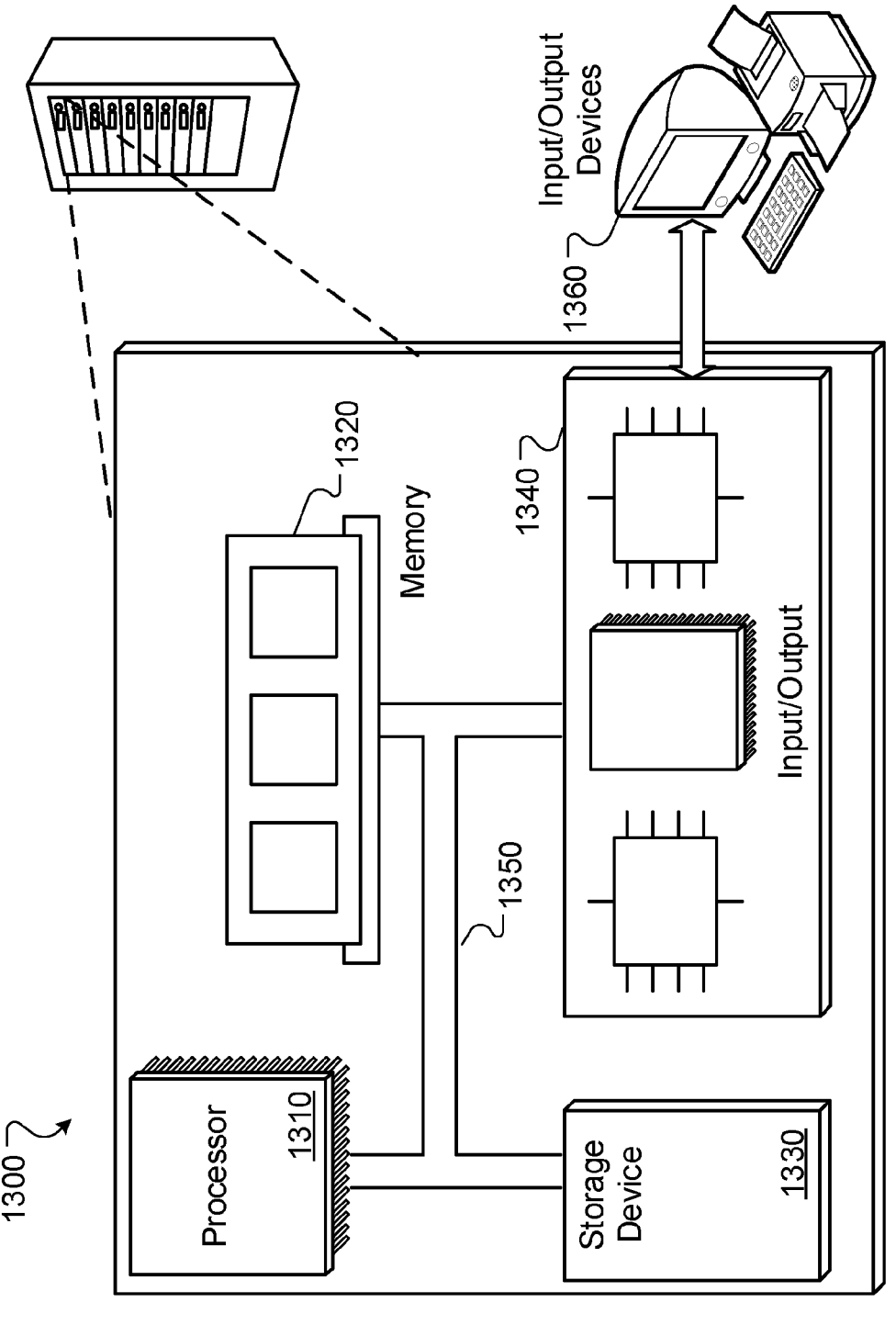
FIG. 13 is a diagram of an example computing system.

FIG. 13 shows an example computer system 1300 that includes a processor 1310, a memory 1320, a storage device 1330 and an input/output device 1340. Each of the components 1310, 1320, 1330 and 1340 can be interconnected, for example, by a system bus 1350. The processor 1310 is capable of processing instructions for execution within the system 1300. In some implementations, the processor 1310 is a single-threaded processor, a multi-threaded processor, or another type of processor. The processor 1310 is capable of processing instructions stored in the memory 1320 or on the storage device 1330. The memory 1320 and the storage device 1330 can store information within the system 1300.

The input/output device 1340 provides input/output operations for the system 1300. In some implementations, the input/output device 1340 can include one or more of a network interface device, e.g., an Ethernet card, a serial communication device, e.g., an RS-232 port, and/or a wireless interface device, e.g., an 802.11 card, a 3G wireless modem, a 4G wireless modem, a 5G wireless modem, etc. In some implementations, the input/output device can include driver devices configured to receive input data and send output data to other input/output devices, e.g., keyboard, printer and display devices 1360. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of embodiments have been described. For example, the detailed description and the accompanying drawings to which it refers are intended to describe some, but not necessarily all, examples or embodiments of the system. The described embodiments are to be considered in all respects only as illustrative and not restrictive. Nevertheless, it will be understood that various modifications may be made without departing from the spirit and scope of the data processing system described herein. Accordingly, other embodiments are within the scope of the following claims.

What is claimed is:

1. A temperature management system for controlling a temperature of a body of a patient and for determining a value indicative of a thermoregulatory activity of the patient, the system comprising:

a heat exchange system comprising:
a heat exchange device,
an extracorporeal control console, and
a fluid reservoir for storing a cooling fluid,
the heat exchange system configured to exchange heat with the body of the patient and to record operational data while controlling the temperature of the body of the patient;

a sensor configured to measure temperature data indicative of a temperature of the body of the patient;

a user interface configured to receive user input and emit at least one of a visual alert and audible alert; and a processor, a memory storing instructions, and associated circuitry communicatively coupled to the sensor, wherein the processor is configured to:
receive the temperature data from the sensor indicative of the temperature of the body of the patient;
control, based on the temperature data, the heat exchange system to maintain the temperature of the body of the patient within a target temperature range;
obtain in response to the controlling, the operational data including a value of the temperature of the cooling fluid in the fluid reservoir;
determine, based on the value, a trend for values of the temperature of the fluid reservoir;
determine, based on the temperature data and the trend of the values, the value indicative of the thermoregulatory activity of the patient; and
generate, based on the value, an alert through the user interface indicating the thermoregulatory activity of the patient.

2. The system of claim 1, wherein the alert comprises a score, the score being indicative of a patient presenting an underlying hyperthermic state or hypothermic state.

3. The system of claim 2, wherein the alert comprises a score, the score being indicative of the patient having a damaged or compromised endogenous thermoregulatory mechanism.

4. The system of claim 1, wherein the processor is further configured to determine an effectiveness of an endogenous thermoregulatory mechanism of the patient in changing the temperature of the body of the patient.

5. The system of claim 1, wherein the value represents cooling power required to change the temperature of the body of the patient a number of degrees over a predefined time interval, the number of degrees being indicative of an effectiveness of an endogenous thermoregulatory mechanism of the patient.

6. The system of claim 1, wherein the heat exchange device comprises an intravascular heat exchange catheter or a heat exchange surface pad for exchanging heat with the patient.

7. The system of claim 1, wherein the processor is configured, in response to determining the value indicative of the thermoregulatory activity, to cause a therapeutic response by the heat exchange system or another device or system for treating the thermoregulatory activity of the patient.

8. The system of claim 1, further comprising a catheter coupled to the sensor, and wherein the sensor is configured to measure a blood temperature of the patient.

9. The system of claim 8, wherein the processor is configured to determine a mass flow rate based on a change in blood temperature over time.

10. The system of claim 9, wherein the processor is configured to determine a cardiac output value of the patient based on the mass flow rate; and
wherein generating the alert indicating the thermoregulatory activity of the patient is based on the cardiac output value of the patient exceeding a threshold cardiac output value.

11. The system of claim 1, wherein the processor is further configured to:
receive training data comprising a plurality of measurements of a first type of operational data for a plurality of patients;
determine, based on the training data, a relationship between the first type of operational data of the heat exchange system and the thermoregulatory activity of the patient; and
adjust one or more thresholds associated with the first type of operational data for generating the alert indicating the thermoregulatory activity of the patient based on the relationship.

12. The system of claim 1, wherein determining the value indicative of the thermoregulatory activity of the patient comprises:
receiving, at machine learning logic, two or more types of the operational data; and
applying the machine learning logic to the two or more types of the operational data.

13. The system of claim 1, wherein determining the trend for the values of the temperature of the fluid reservoir comprises determining that the values represent i) an increase of the temperature of the fluid reservoir over time, ii) a decrease of the temperature of the fluid over time, or iii) an oscillation of one or more of temperature of the fluid reservoir over time;
determining that a rate of change of the values represented by the increase, the decrease, or the oscillation satisfies a threshold; and
determining, based on satisfying the threshold, the value indicative of the thermoregulatory activity of the patient.

14. A temperature management system for controlling a temperature of a body of a patient and for determining a value indicative of a thermoregulatory activity of the patient, the system comprising:
a heat exchange system comprising a heat exchange device, an extracorporeal control console, and a fluid reservoir for storing a cooling fluid, the heat exchange system configured to exchange heat with the body of the patient and to record operational data representing operation of the heat exchange device while controlling the temperature of the body of the patient, wherein the operational data comprise a fluid reservoir temperature value associated with the fluid reservoir of the heat exchange system;
a user interface configured to receive user input and emit at least one of a visual alert and audible alert; and a processor, a memory storing instructions, and associated circuitry communicatively coupled to the heat exchange system, wherein the processor is configured to:

obtain a value of the temperature of the cooling fluid in the fluid reservoir;

determine a trend for values of the temperature of the fluid reservoir;

determine a value indicative of a thermoregulatory activity of the patient based on the trend for the values; and in response to determining the value, cause a therapeutic response by the heat exchange system or an additional device or system for treating the thermoregulatory activity of the patient.

15. The system of claim 14, wherein the therapeutic response by the heat exchange system or another device or system comprises an automatic injection or infusion of a supplemental fluid.

16. The system of claim 15, where the automatic injection or infusion is an injection or infusion of an anti-shivering medication.

17. The system of claim 14, wherein determining the value indicative of the thermoregulatory activity of the patient comprises:

receiving, at machine learning logic, two or more types of the operational data; and applying the machine learning logic to the two or more types of the operational data.

18. A method for controlling a temperature of a body of a patient and for determining a value indicative of a thermoregulatory activity of the patient, the method comprising:

receiving, by a processor, temperature data from a sensor indicative of the temperature of the body of the patient;

receiving, by the processor from a set of sensors, operational data representing a temperature of cooling fluid in a fluid reservoir;

controlling, by the processor based on the temperature data, a heat exchange system to maintain the temperature of the body of the patient within a target temperature range, the heat exchange system being configured to exchange heat with the body of the patient and to record operational data representing operation of the heat exchange system while controlling the temperature of the body of the patient, the operational data comprising a fluid reservoir temperature value associated with a fluid reservoir for storing a cooling fluid;

receiving, by the processor in response to the controlling, a value of the temperature of the cooling fluid in the fluid reservoir;

determining a trend for values of the temperature of the fluid reservoir;

determining, based on the temperature data and the trend of the values, a value indicative of a thermoregulatory activity of the patient; and generating, by the processor and based on the value indicative of the thermoregulatory activity, an alert indicating the thermoregulatory activity of the patient.

19. The method of claim 18, wherein the alert comprises a score, the score being indicative of a patient presenting an underlying hyperthermic state or hypothermic state.

20. The method of claim 18, wherein determining the value indicative of the thermoregulatory activity of the patient comprises:

receiving, at machine learning logic, two or more types of the operational data; and applying the machine learning logic to the two or more types of the operational data.

* * * * *